United States Patent
Slaughter et al.

(10) Patent No.: US 10,898,202 B2
(45) Date of Patent: Jan. 26, 2021

(54) ATRIAL APPENDAGE CLOSURE DEVICE AND RELATED METHODS

(71) Applicant: UNIVERSITY OF LOUISVILLE RESEARCH FOUNDATION, INC., Louisville, KY (US)

(72) Inventors: Mark S. Slaughter, Louisville, KY (US); Guruprasad A. Giridharan, Louisville, KY (US); Steven C. Koenig, Floyds Knobs, IN (US); Michael A. Sobieski, Floyds Knobs, IN (US); Kevin Soucy, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 116 days.

(21) Appl. No.: 15/754,708

(22) PCT Filed: Aug. 25, 2016

(86) PCT No.: PCT/US2016/048713
§ 371 (c)(1),
(2) Date: Feb. 23, 2018

(87) PCT Pub. No.: WO2017/035363
PCT Pub. Date: Mar. 2, 2017

(65) Prior Publication Data
US 2018/0235640 A1 Aug. 23, 2018

Related U.S. Application Data

(60) Provisional application No. 62/209,657, filed on Aug. 25, 2015, provisional application No. 62/313,341, filed on Mar. 25, 2016.

(51) Int. Cl.
*A61B 17/12* (2006.01)
*A61B 17/064* (2006.01)
*A61B 17/00* (2006.01)

(52) U.S. Cl.
CPC ...... *A61B 17/12122* (2013.01); *A61B 17/064* (2013.01); *A61B 17/12031* (2013.01);
(Continued)

(58) Field of Classification Search
CPC ........ A61B 17/12122; A61B 17/12177; A61B 17/12031; A61B 17/12172
See application file for complete search history.

(56) References Cited

U.S. PATENT DOCUMENTS 6,551,303 B1 * 4/2003 Van Tassel ......... A61B 17/0057 128/898
6,652,556 B1 * 11/2003 VanTassel ........ A61B 17/12159 606/200

(Continued)

FOREIGN PATENT DOCUMENTS

| WO | 00/27292 | 5/2000 |
| WO | 2008/150346 | 12/2008 |
| WO | 2014/018907 | 1/2014 |

*Primary Examiner* — Richard G Louis
(74) *Attorney, Agent, or Firm* — W & C IP

(57) ABSTRACT

An atrial appendage closure device is provided that includes an occluding portion having a distal surface and a proximal surface opposite the distal surface, the occluding portion being moveable between a retracted position and a deployed position such that, in the deployed position, the occluding portion is configured to provide a seal between a left atrial appendage and a left atrium of a heart. An anchoring portion is operably connected to the occluding member with the anchoring portion being moveable between a retracted position and a deployed position. Methods for occluding a left atrial appendage that make use of the closure devices are also provided.

12 Claims, 33 Drawing Sheets

(52) U.S. Cl.
CPC .. *A61B 17/12172* (2013.01); *A61B 17/12177* (2013.01); *A61B 2017/00292* (2013.01); *A61B 2017/0641* (2013.01); *A61B 2017/0649* (2013.01); *A61B 2017/1205* (2013.01)

(56) References Cited

U.S. PATENT DOCUMENTS

| | | | |
|---|---|---|---|
| 7,128,073 | B1 | 10/2006 | Van Der Burg |
| 2004/0034366 | A1* | 2/2004 | van der Burg ............ A61F 2/01 606/119 |
| 2004/0098031 | A1* | 5/2004 | van der Burg ... A61B 17/12122 606/200 |
| 2005/0043759 | A1* | 2/2005 | Chanduszko ...... A61B 17/0057 606/213 |
| 2007/0083230 | A1* | 4/2007 | Javois ............. A61B 17/12172 606/213 |
| 2008/0015636 | A1* | 1/2008 | Olsen ................ A61B 17/0057 606/213 |
| 2015/0005810 | A1* | 1/2015 | Center ............. A61B 17/12172 606/200 |

* cited by examiner

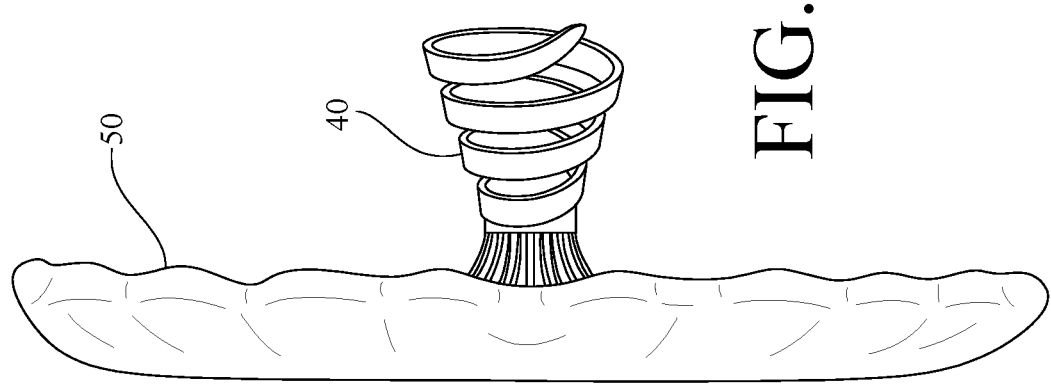
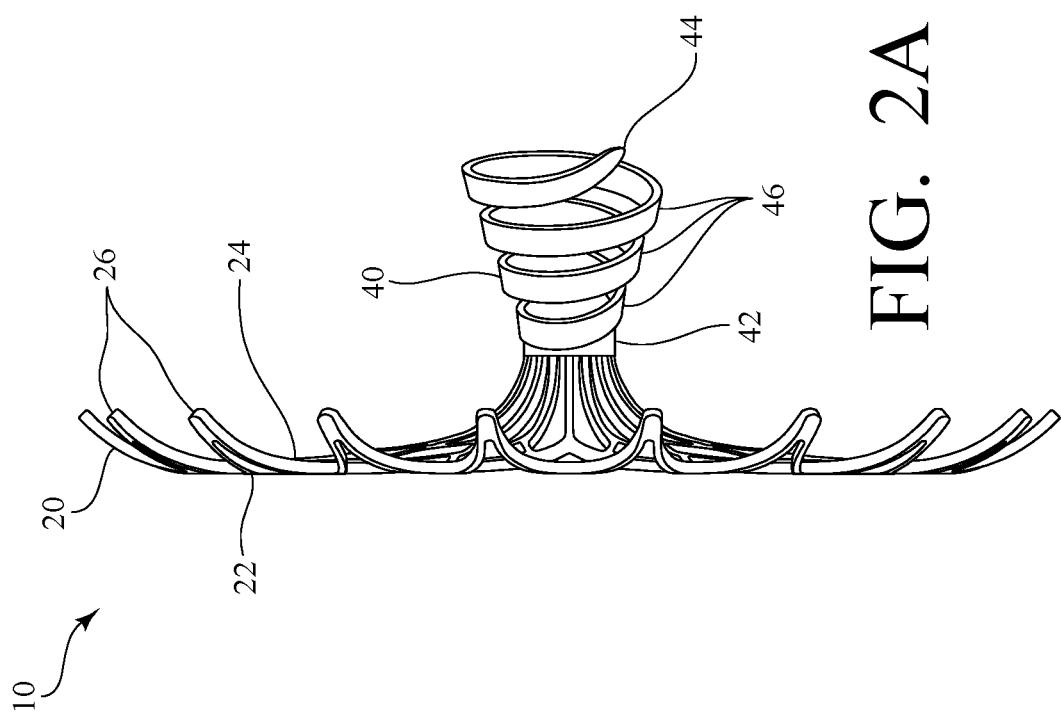

ATRIAL APPENDAGE CLOSURE DEVICE AND RELATED METHODS

RELATED APPLICATIONS

This application claims priority to U.S. Provisional Application Ser. No. 62/313,341, filed Mar. 25, 2016 and U.S. Provisional Application Ser. No. 62/209,657, filed Aug. 25, 2015, the entire disclosures of which are incorporated herein by this reference.

TECHNICAL FIELD

The presently-disclosed subject matter relates to an atrial appendage closure device. In particular, the presently-disclosed subject matter relates to an atrial appendage closure device having an occluding portion, which, in a deployed position, is configured to occlude and provide a seal between a left atrial appendage and a left atrium of a heart.

BACKGROUND

In the United States, there are approximately three million patients with atrial fibrillation (AF), and this number is expected to increase to five million by 2040. AF is an irregular sinus rhythm and atrial dysrhythmia, which results in a rapid, irregular, and unsynchronized contraction of the atrium. In AF, blood is not washed from the left atrial appendage and it stagnates and tends to clot inside the heart. However, these clots are prone to leaving the heart and embolizing to different organs in the body. For example, it has been observed that the clots frequently leave the heart and enter the cerebral vessels, resulting in an embolic stroke. Indeed, patients with AF are at a significantly increased risk of stroke, and it is estimated that patients with AF have, on average, 5 to 6 times greater probability of having a stroke (5-15% annualized risk of stroke) and 18 times greater probability of having an embolic event. This risk of stroke with AF only increases with age, with up to 30% of all strokes in elderly patients occurring due to AF, and with, overall, at least 100,000 strokes per year being attributed to AF in the United States alone.

Medical and ablation therapies have been used to attempt to eliminate AF, but most patients continue to remain in AF after therapy. In this regard, current treatment of AF often includes anticoagulation therapy with warfarin, which has been reported to reduce the risk of stroke by 62%, but requires close monitoring to prevent bleeding complications that may otherwise result in mortality. In fact, even with close attention to warfarin dosing, life-threatening bleeding complications, intracerebral bleeding, or death still occurs in 1-2.5% of these patients every year, with the highest risk of warfarin complications being in elderly patients, who are also at the highest risk of stroke due to AF. Due to this risk, it is estimated that 40% to 65% of elderly patients with AF and at an increased risk of stroke are not receiving anticoagulant therapy with warfarin. However, it has further been estimated that 35% of patients with AF who are not treated with anticoagulants will likely have a stroke during their lifetime.

Antiplatelet therapy with aspirin has been proposed as a possible alternative to warfarin therapy, but to date has not proven to be very effective. Similarly, combination therapy with aspirin and clopidogrel has also not proven to be as effective in preventing clot formation as warfarin. New pharmaceutical agents aimed at factor Xa and thrombin inhibition anticoagulant agents, such as Pradaxa® (Boehringer Ingelheim Pharma GmbH & Co. KG; dabigatran etexilate) have provided similar reductions in stroke rates and less monitoring when compared to warfarin. Nevertheless, many of these agents, including Pradaxa® are contraindicated for patients over 75, have been shown to still result in bleeding complications, and still require compliance from elderly patients who often forget to take their oral medications.

To overcome these limitations of pharmaceutical agent-based therapies for treating AF, catheter-based left atrial appendage occluder devices, such as AMPLATZER® (AGA Medical Corporation), PLAATO® (EV3 Inc.), and WATCHMAN® (Atritech, Inc.), as well as other devices such as the TIGERPAW® system (LAAx, Inc.) and ATRICLIP® (AtriCure, Inc.), have recently been developed. Initial reports regarding the use of these device-based therapies to block the left atrial appendage have provided good results, and have shown that the devices can reduce hemorrhagic stroke as compared to warfarin therapy. However, recent clinical trials with these devices have also shown an associated increase in ischemic stroke, which is in addition to the fact that the implantation of the devices requires a delivery catheter to puncture the atrial septum as well as barbs for anchoring the devices, both of which can lead to several complications including puncturing of the left atrium. Moreover, these current left atrial appendage closure devices are not always completely effective in sealing off the left atrial appendage due to patient-to-patient variability in left atrial appendage sizes, thus leading to embolic clots. Further, it is also possible that any foreign material in the left atrial appendage may also cause thrombus formation. Accordingly, an atrial appendage closure device that avoids the adverse events common with current catheter-based left atrial appendage occluder devices or common with current pharmaceutical therapies would be both highly-desirable and beneficial.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter includes an atrial appendage closure device. In particular, the presently-disclosed subject matter includes an atrial appendage closure device having an occluding portion, which, in a deployed position, is configured to occlude and provide a seal between a left atrial appendage and a left atrium of a heart.

In one exemplary embodiment of the presently-disclosed subject matter, an exemplary atrial appendage closure device made in accordance with the present invention includes an occluding portion having a distal surface and a proximal surface opposite the distal surface. The atrial appendage closure device further includes an anchoring portion having a proximal end connected to the proximal surface of the occluding portion and a distal end positioned away from the proximal surface of the occluding portion. The anchoring portion is generally shaped like a corkscrew and provides the means to secure the occluding portion when implanted, as further discussed below.

The occluding portion is moveable between a retracted position and a deployed position. Specifically, when the occluding is in the deployed position, it extends outward to form a substantially flat disc with the anchoring portion connected to the center of the proximal surface of the occluding portion and extending outward substantially perpendicular to the occluding portion. In other words, when the occluding portion is in the deployed position, the distal surface of the occluding portion is substantially perpendicular to the anchoring portion, and similarly, the proximal surface of the occluding portion is substantially perpendicular to the anchoring portion. By contrast, when the occluding portion is in the retracted position, the occluding portion is collapsed away from the anchoring portion such that the proximal surface of the occluding portion is at an obtuse angle relative to the anchoring portion and such that the distal surface of the occluding portion effectively defines a cavity.

To facilitate the movement of the occluding portion between the retracted position and the deployed position, the occluding portion is comprised of a collapsible frame in a starburst pattern. An exemplary starburst pattern is a diamond mesh comprising a plurality of interconnected members that form a repeating pattern of substantially diamond shaped openings in the occluding portion. The starburst pattern terminates at the perimeter of the occluding portion in a plurality of curved tips that curve in a direction extending from the distal surface of the occluding portion towards the proximal surface of the occluding portion.

The starburst pattern of the occluding portion provides sufficient flexibility such that the occluding portion can be collapsed into the retracted position for insertion of the occluding portion into a heart and subsequently expanded into the deployed position upon insertion of the occluding portion, as further discussed below. Furthermore, by constructing the occluding portion as a collapsible frame in a starburst pattern, the occluding portion can accommodate anatomical variability between subjects and allow the device to effectively seal off a left atrial appendage upon implantation, as also further discussed below.

The anchoring portion is an expandable conical coil that, like the occluding portion is movable between a retracted position and an expanded position. In particular, the anchoring portion is comprised of one or more helical turns extending between the proximal end and the distal end of the anchoring portion with each of the one or more helical turns having a diameter. In the deployed position, the diameter of the one or more helical turns progressively increases as the one or more helical turns extend from the proximal end of the anchoring portion to the distal end of the anchoring portion. By comparison, in the retracted position, the diameter of each of the one or more helical turns is substantially the same.

Because the occluding portion and the anchoring portion are both capable of being expanded and collapsed between retracted and deployed positions, it is contemplated that the exemplary atrial appendage closure device can be implanted into a subject via a catheter-based delivery system. In an exemplary embodiment the proximal surface of the occluding portion is pressed against the interior surface of the catheter and the one or more helical turns of the anchoring portion are similarly pressed against the interior surface of the catheter. As such, both the occluding portion and the anchoring portion are restrained by the catheter and biased in the retracted position when inside the catheter. As such, upon exiting the catheter, the occluding portion and the anchoring portion will automatically move from the retracted position to the deployed position.

In some embodiments, the occluding portion can also be covered by a flexible material or membrane that is supported by the collapsible frame. The membrane is flexible enough to be capable of moving along with the frame of the occluding portion between the retracted position and the deployed position, but the membrane is still sufficiently rigid such that the device can provide an effective seal between the left atrial appendage and left atrium of a heart and the membrane will not collapse into the left atrial appendage upon being exposed to the blood flow in the heart and the pressure generated by the left atrium. In some embodiments, the membrane is configured so as to promote epithelialization or, in other words, to promote the deposition of epithelial cells and the growth of an epithelial cell layer over the membrane. To this end, the membrane is generally comprised of a biocompatible material. Biocompatible materials suitable for use in the present invention include, but are not limited to, polytetrafluoroethylene, polyethylene terephthalate or Dacron® (manufactured and supplied by E.I. duPont de Nemours and Co., Inc.). Furthermore, it is contemplated that the biocompatible materials can be provided in a variety of suitable forms including, for example, a velour.

To further facilitate the use of the atrial appendix closure devices of the presently-disclosed subject matter and promote the integration of the devices into the heart of a subject, the outer surface, the inner surface, or both the outer surface and the inner surface of the occluding member are coated with an extracellular matrix. In some embodiments, to facilitate the use of the devices and promote their integration, the outer surface, the inner surface, or both the outer surface and the inner surface of the occluding member are coated with a growth factor.

Further provided by the presently-disclosed subject matter are methods of occluding a left atrial appendage. In one exemplary implementation of a method of occluding a left atrial appendage, an atrial appendage closure device is first provided and positioned within a catheter with the occluding portion and the anchoring portion both in a retracted position. Next, the atrial appendage closure device is implanted using a transseptal approach via the femoral vein of a subject using an over the guidewire, modified Seldinger's technique until the catheter is positioned within the left atrium adjacent to the left atrial appendage with the end of the catheter positioned within the orifice of the left atrial appendage. The atrial appendage closure device is then extended forward out of the catheter, unsheathing the anchoring portion and allowing the anchoring portion to deploy with the distal end of the anchoring portion immediately adjacent to the interior of a remote wall of the left atrial appendage, which is positioned away from the orifice of the left atrial appendage. The atrial appendage device is next rotated causing the anchoring portion to screw into the wall of the left atrial appendage securing the anchoring portion to the remote wall of the left atrial appendage.

After the anchoring portion is secured to the remote wall of the left atrial appendage, the catheter, with the occluding portion of the atrial appendage closure device still contained within, is pulled backward until the catheter is positioned entirely within the left atrium, thereby pulling the remote wall of the left atrial appendage until it is positioned adjacent to the orifice of the left atrial appendage and the left atrial appendage is completely collapsed. The occluding portion of the device is subsequently removed from the catheter so that the occluding portion is deployed inside the left atrium, forming a seal across the orifice of the left atrial appendage. The occluding portion is sized such that once it is in the deployed position, it cannot pass through the orifice of the left atrial appendage. As such, and because the occluding portion is connected to the anchoring portion which itself is secured to the remote wall of the left atrial appendage, the device keeps the left atrial appendage collapsed and effectively occludes the left atrial appendage. The catheter is then withdrawn, leaving the device implanted in the heart.

Further features and advantages of the presently-disclosed subject matter will become evident to those of ordinary skill in the art after a study of the description, figures, and non-limiting examples in this document.

BRIEF DESCRIPTION OF THE DRAWINGS

FIG. 2A is a side view of the atrial appendage closure device of FIG. 1A;

FIG. 2B is a side view of the atrial appendage closure device of FIG. 1A and further covered with a membrane;

DESCRIPTION OF EXEMPLARY EMBODIMENTS

The presently-disclosed subject matter includes an atrial appendage closure device and, more particularly, an atrial appendage closure device having an occluding portion, which, in a deployed position, is configured to occlude and provide a seal between a left atrial appendage and a left atrium of a heart.

Figure 1A:
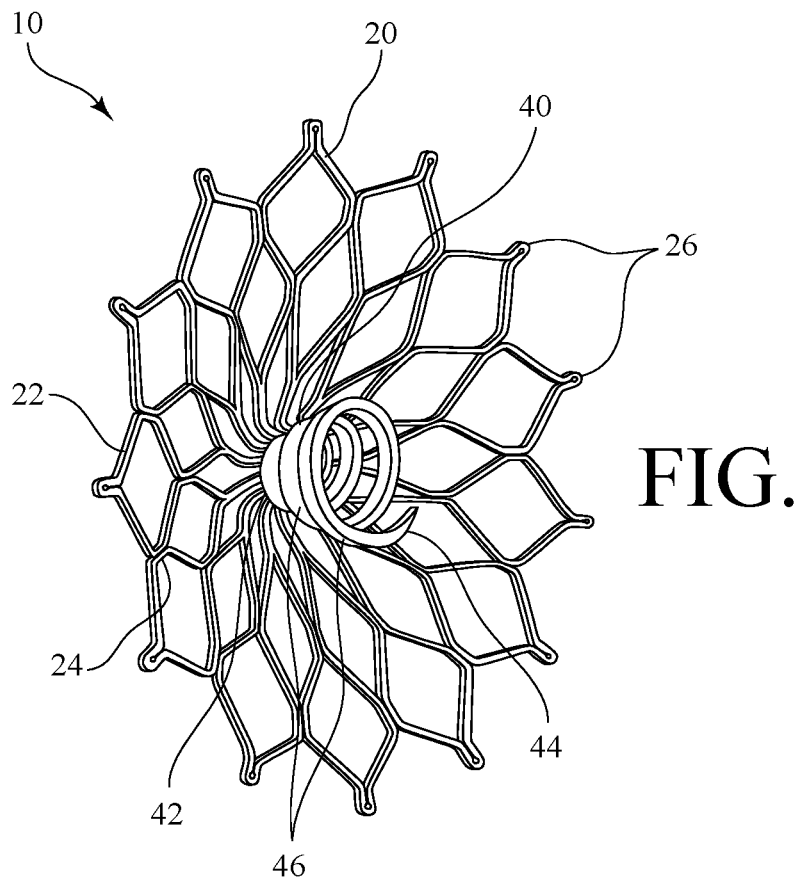
FIG. 1A is a perspective view of an exemplary atrial appendage closure device made in accordance with the present invention and including an occluding portion in a deployed position and an anchoring portion in a deployed position.
Figure 3:
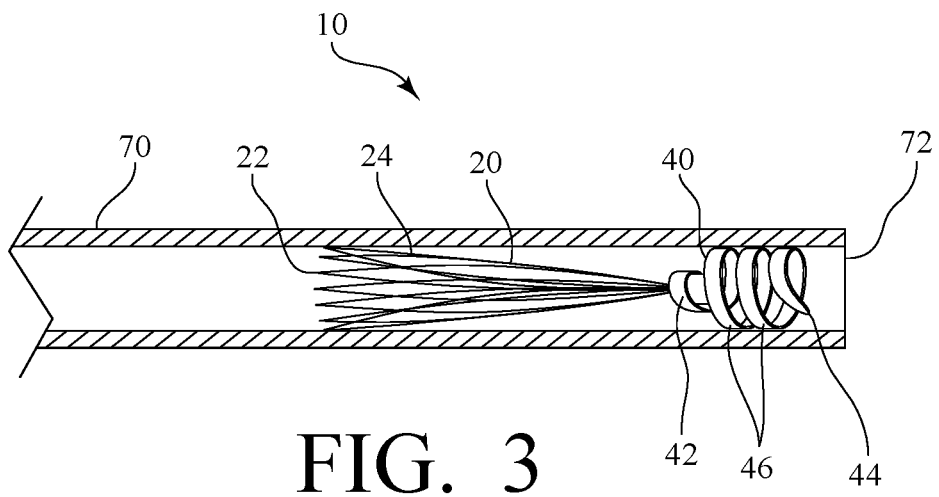
FIG. 3 is a side view of the atrial appendage closure device of FIG. 1 positioned within a delivery catheter and with the occluding portion schematically represented in a rearward facing retracted position and the anchoring portion in a retracted position.

Referring first to FIGS. 1A, 2A, and 3, an exemplary atrial appendage closure device 10 made in accordance with the present invention includes an occluding portion 20 having a distal surface 22 and a proximal surface 24 opposite the distal surface 22. The atrial appendage closure device 10 further includes an anchoring portion 40 having a proximal end 42 connected to the proximal surface 24 of the occluding portion 20 and a distal end 44 positioned away from the proximal surface 24 of the occluding portion 20. The anchoring portion 40 is generally shaped like a corkscrew and provides the means to secure the occluding portion 20 when implanted, as further discussed below.

With regard to the occluding portion 20, and referring now also to FIG. 3, the occluding portion 20 is moveable between a retracted position (shown in FIG. 3) and a deployed position (shown in FIGS. 1A, and 2A). Specifically, as best shown in FIG. 2A, when the occluding portion 20 is in the deployed position, it extends outward to form a substantially flat disc. The anchoring portion 40 is connected to the center of the proximal surface 24 of the occluding portion 20 and extends outward substantially perpendicular to the occluding portion 20. In other words, when the occluding portion 20 is in the deployed position, the distal surface 22 of the occluding portion 20 is substantially perpendicular to the anchoring portion 40, and similarly, the proximal surface 24 of the occluding portion 20 is substantially perpendicular to the anchoring portion 40. Of course, the occluding portion 20 need not be fully or substantially perpendicular to the anchoring portion 40 when in the deployed position. In some embodiments, when the occluding portion 20 is in the deployed position, the occluding portion 20 can be partially collapsed towards the anchoring portion 40 such that the proximal surface 24 of the occluding portion 20 is at an acute angle to the anchoring portion 40. In some other embodiments, when the occluding portion 20 is in the deployed position, the occluding portion 20 is partially collapsed away from the anchoring portion 40 such that the proximal surface 24 of the occluding portion 20 is at an obtuse angle to the anchoring portion 40. Furthermore, in certain embodiments, it is contemplated that the angle of the occluding portion 20 relative to the anchoring portion 40 can be adjustable through the use of a gimbal or other mechanism known to those of ordinary skill in the art.

As shown in FIG. 3, which shows the device 10 positioned within a catheter 70, when the occluding portion 20 is in the retracted position, the occluding portion 20 is collapsed away from the anchoring portion 40 facing towards the open end 72 of the delivery catheter 172 such that the proximal surface 24 of the occluding portion 20 is at an obtuse angle to the anchoring portion 40 and the distal surface 22 of the occluding portion 20 effectively defines a cavity.

To facilitate the movement of the occluding portion 20 between the retracted position and the deployed position, the occluding portion 20 is comprised of a collapsible frame in a starburst pattern. In particular, as best shown in FIG. 1A, the starburst pattern of the exemplary occluding portion 20 is a diamond-mesh comprising a plurality of interconnected members that form a repeating pattern of substantially diamond shaped openings in the occluding portion 20. The starburst pattern terminates at the perimeter of the occluding portion 20 in a plurality (thirteen) of curved tips 26 that, as perhaps best shown in FIG. 2A, curve in a direction extending from the distal surface 22 of the occluding portion 20 towards the proximal surface 24 of the occluding portion 20. These curved tips 26 help secure the occluding portion 20 once the occluding portion 20 is in place and effectively seal off a left atrial appendage upon implantation, as further discussed below. Of course, in other embodiments the number of curved tips can vary without departing from the spirit and scope of the present invention, and, in some cases, there may not be any curved tips whatsoever.

The starburst pattern of the occluding portion 20 provides sufficient flexibility such that the occluding portion 20 can be collapsed in the retracted position for insertion of the occluding portion 20 into a heart and then subsequently expanded into the deployed position upon insertion of the occluding portion 20, as further discussed below. Furthermore, by constructing the occluding portion 20 as a collapsible frame in a starburst pattern, the occluding portion 20 can accommodate anatomical variability between subjects and allow the device 10 to effectively seal off a left atrial appendage upon implantation, as also further discussed below.

With regard to the anchoring portion 40, and referring once again to FIGS. 1A, 2A, and 3, the anchoring portion 40 is an expandable conical coil that, like the occluding portion 20 is movable between a retracted position and an expanded position. In particular, the anchoring portion 40 is comprised of one or more helical turns 46 extending between the proximal end 42 and the distal end 44 of the anchoring portion 40 with each of the one or more helical turns 46 having a diameter. As perhaps best shown in FIG. 2A, in the deployed position, the diameter of the one or more helical turns 46 progressively increases as the one or more helical turns 46 extend from the proximal end 42 of the anchoring portion 40 to the distal end 44 of the anchoring portion 40. By comparison, as shown in FIG. 3, in the retracted position, the diameter of each of the one or more helical turns 46 is substantially the same. Furthermore, as shown in FIGS. 1A, 2A and 3, the distal end 44 of the anchoring portion 40 is pointed which provides improved penetration of the anchoring portion 40, as further discussed below.

Regardless of the particular configuration of the occluding portion 20 and the anchoring portion 40, it is contemplated that the occluding portion 20 and the anchoring portion 40 are both comprised of a flexible material to thereby provide a structure that is capable of being moved between a retracted and deployed position, but yet is still sufficiently rigid enough to provide an effective seal between the left atrial appendage and left atrium of a heart. In some embodiments, the occluding portion 20 and the anchoring portion 40 are comprised of a plastic, a metal, a shape memory alloy, or combinations thereof. More specifically, in at least some embodiments, the occluding portion, the anchoring portion, or both the occluding portion and the anchoring portion are comprised of a shape memory alloy, such as, for example, nitinol. In some particular embodiments, the occluding portion and the anchoring portion are both cut from a single nitinol tube using methods known to those of ordinary skill in the art.

Because the occluding portion 20 and the anchoring portion 40 are both capable of being expanded and collapsed between retracted and deployed positions, it is contemplated that the exemplary atrial appendage closure device 10 can be implanted into a subject via a catheter-based delivery system.

For example, in the exemplary embodiment shown in FIG. 3, the proximal surface 24 of the occluding portion 20 is pressed against the interior surface of the catheter 70 and the one or more helical turns 46 of the anchoring portion 40 are similarly pressed against the interior surface of the catheter 70. As such, both the occluding portion 20 and the anchoring portion 40 are restrained by the catheter 70 and biased in the retracted position when inside the catheter 70. As such, upon exiting the open end 72 of the catheter 70, the occluding portion 20 and the anchoring portion 40 will automatically move from the retracted position to the deployed position. In other embodiments, however, it is contemplated that the occluding portion, the anchoring portion, or both can be configured so that they remain in the retracted position regardless of their position within the catheter. In such embodiments, it is contemplated that some other mechanism operably moves the occluding portion or the anchoring portion from the retracted position into the deployed position. For example, in an embodiment where the occluding portion or the anchoring portion is made of shape memory alloy, the deployed position could be set as the "pre-deformation" state of the shape memory alloy such that, after deforming the shape memory alloy into the retracted position, heat is applied and the shape memory alloy "returns" to the deployed position.

Referring now to FIGS. 4A-4I, in an exemplary implementation of the method of occluding a left atrial appendage of a heart of the present invention, an atrial appendage closure device 10 is first provided and positioned within a catheter 70 with the occluding portion 20 and the anchoring portion 40 both in a retracted position, as shown in FIG. 3.

Figure 4A:
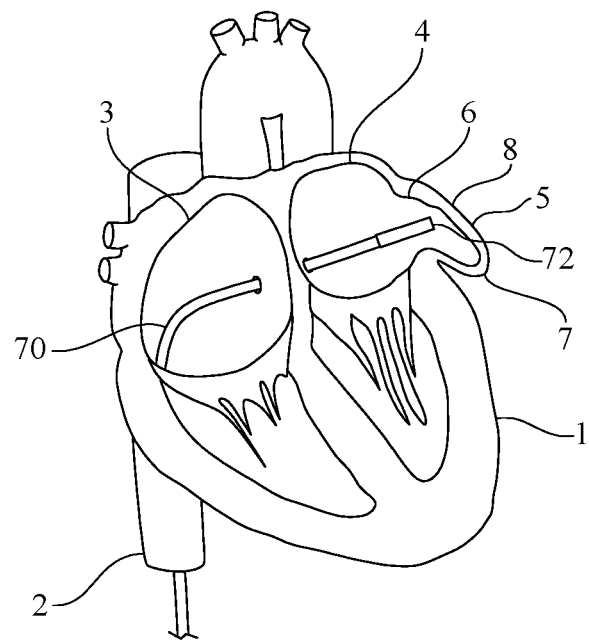
FIGS. 4A-4I are a series of schematic representations of an exemplary method of occluding a left atrial appendage in accordance with the presently-disclosed subject matter, in which the atrial appendage closure device of FIG. 1 is deployed to provide a seal between the left atrial appendage and the left atrium of a heart.

Next, as shown in FIG. 4A, the atrial appendage closure device 10 is implanted using a transseptal approach via the femoral vein of a subject using an over the guidewire, modified Seldinger's technique. More specifically, after the initial venous insertion, the catheter 70 that surrounds the device 10 is first advanced into the right atrium 3 of the heart 1 through the posterior vena cava 2 and then introduced from the right atrium 3 to the left atrium 4 through a transseptal puncture. As shown in FIG. 4A, the catheter 70 is positioned within the left atrium 4 adjacent to the left atrial appendage 5 with the end of the catheter 70 positioned within the orifice 6 of the left atrial appendage 5.

Figure 4B:
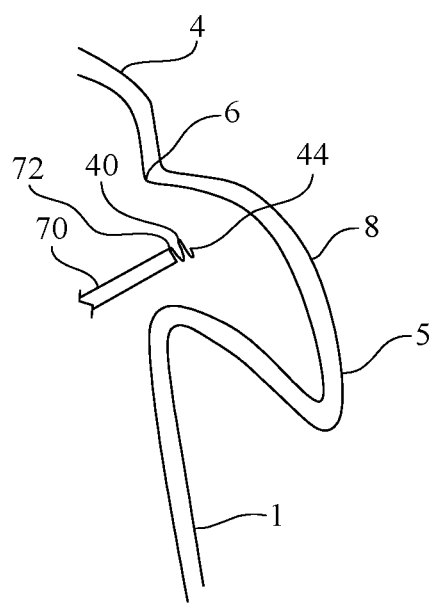
Figure 4C:
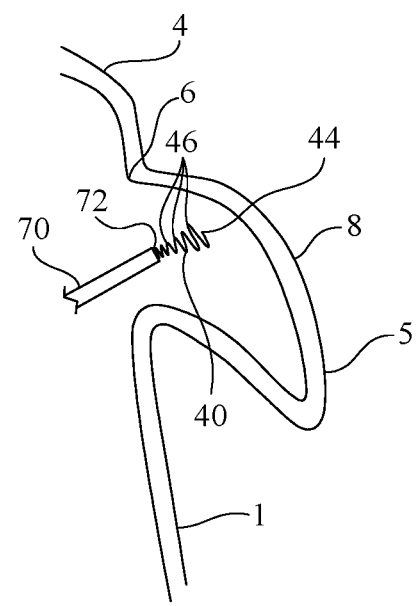
Figure 4D:
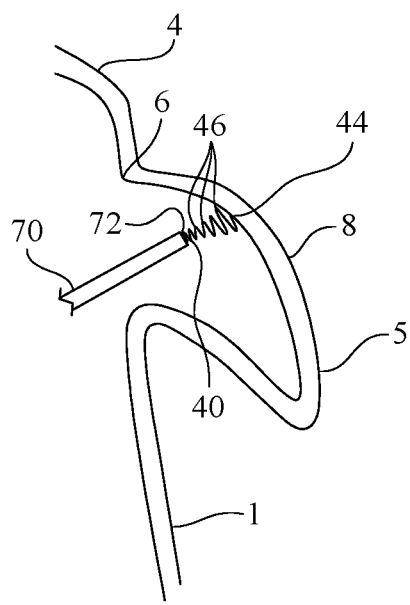

Referring now to FIGS. 4B-4D, after the catheter 70 is positioned within the left atrium 4 adjacent to the left atrial appendage 5, the atrial appendage closure device 10 is extended forward out of the open end 72 of the catheter 70, unsheathing the anchoring portion 40 and allowing the anchoring portion 40 to deploy. That is to say, as the one or more helical turns 46 of the anchoring portion 40 are pushed out of the catheter 70, the diameter of each of the one or more helical turns 46 expands from the diameter of the helical turn 46 in the retracted position (e.g., as shown in FIG. 3) to the diameter of the helical turn 46 in the deployed position (e.g., as shown in FIG. 2A). The catheter 70 and/or the atrial appendage closure device 10 is then extended further forward until, as shown in FIG. 4D, the distal end 44 of the anchoring portion 40 is immediately adjacent to the interior of a remote wall 8 of the left atrial appendage 5, which is positioned away from the orifice 6 of the left atrial appendage 5.

Figure 4E:
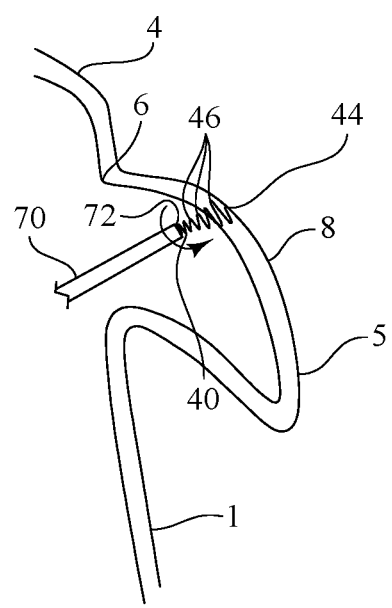
Figure 4F:
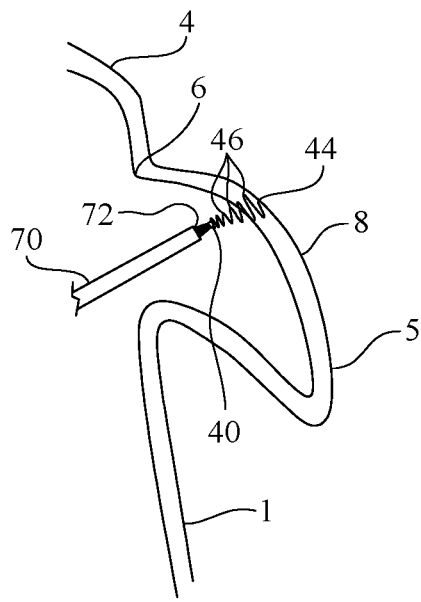

Referring now to FIGS. 4E-4F, the atrial appendage device 10 is next rotated causing the anchoring portion 40 to screw into the wall of the left atrial appendage 5. As previously mentioned, in at least some embodiments, the distal end 44 of the anchoring portion 40 is pointed which provides improved penetration of the anchoring portion 40 through the wall of the left atrial appendage 5. Here, the anchoring portion 40 is connected to the remote wall 8 of the left atrial appendage 5 at an upper portion of the left atrial appendage 5, but it is contemplated that the anchoring portion 40 can be connected to other portions of the left atrial appendage, as further discussed below.

Figure 4G:
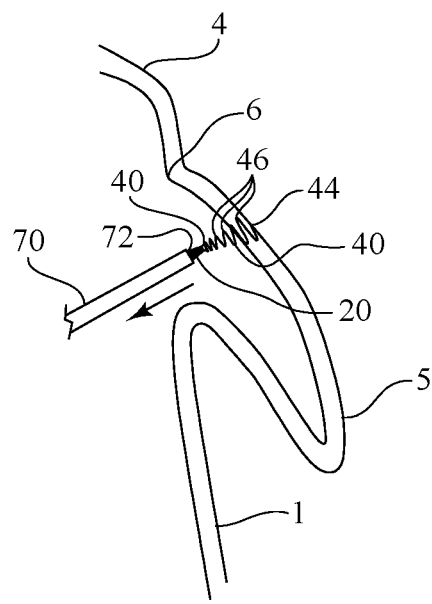
Figure 4H:
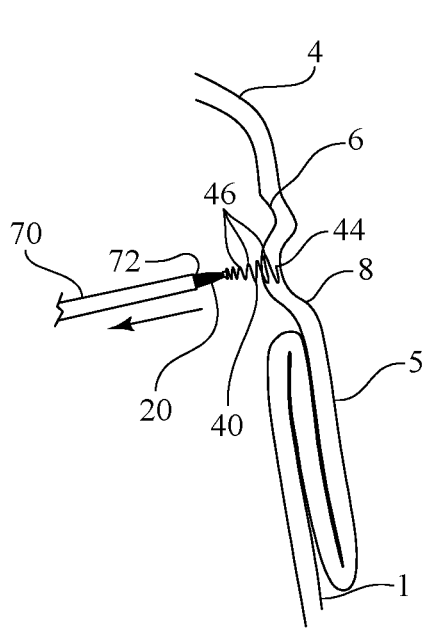

Referring now to FIGS. 4G-4H, after the anchoring portion 40 is secured to the remote wall 8 of the left atrial appendage 5, the catheter 70, with the occluding portion 20 of the atrial appendage closure device 10 still contained within, is pulled backward until the catheter 70 is positioned entirely within the left atrium 4. As shown in FIG. 4H, the remote wall 8 of the left atrial appendage 5 is now positioned adjacent to the orifice 6 of the left atrial appendage 5 and the left atrial appendage 5 is completely collapsed.

Figure 4I:
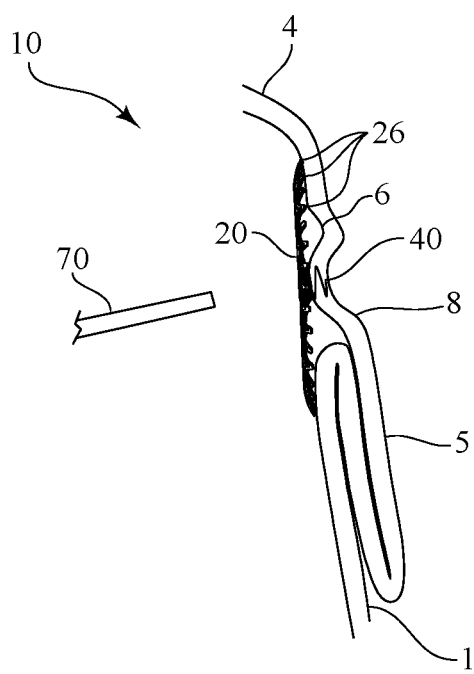

Referring now to FIG. 4I, the occluding portion 20 of the device 10 is subsequently removed from the catheter 70 so that the occluding portion 20 is deployed inside the left atrium 4, forming a seal across the orifice 6 of the left atrial appendage 5. To this end, as shown in FIG. 4I, the plurality of curved tips 26 of the occluding portion 20 act as hooks which latch onto the interior wall of the left atrium 4, keeping the occluding portion 20 secured in place over the orifice 6 of the left atrial appendage 5. Furthermore, the occluding portion 20 is sized such that once the occluding portion 20 is in the deployed position, it cannot pass through the orifice 6 of the left atrial appendage 5. As such, and because the occluding portion 20 is connected to the anchoring portion 40 which itself is secured to the remote wall 8 of the left atrial appendage 5, the device 10 keeps the left atrial appendage 5 collapsed and effectively occludes the left atrial appendage 5. The catheter 70 is then withdrawn, leaving the device 10 implanted in the heart 1.

Of course, it is contemplated that the left atrial appendage 5 need not be completely collapsed. Specifically, depending on the configuration of the appendage closure device 10 after the occluding portion 20 is deployed, the remote wall 8 of the left atrial appendage 5 may not maintain a position immediately next to the orifice 6 of the left atrial appendage 5. For example, if the length of the anchoring portion 40 is greater, or if the anchoring portion 40 is not screwed as deeply into the remote wall 8 of the left atrial appendage 5, after the device 10 is implanted, a space may remain between the remote wall 8 of the left atrial appendage 5 and the orifice 6 of the left atrial appendage 5. To improve occlusion, it is contemplated that the device 10 can include an anchoring portion 40 in one of multiple sizes with the size of the anchoring portion 40 selected based, at least in part, on the thickness of the walls of the left atrium 4 and/or the left atrial appendage 5 of a patient. A non-limiting list of possible lengths of the anchoring portion 40 includes about 4 mm, about 6 mm, and about 8 mm. As used herein, the length of the anchoring portion 40 is the linear distance between the proximal end 42 of the anchoring portion 40 and the distal end 44 of the anchoring portion 40 taken along a longitudinal axis of the anchoring portion 40 extending down the center of the one or more helical turns 46.

As mentioned above, the occluding portion 20 is sized so that it cannot pass through the orifice 6 of the left atrial appendage 5. To this end, it is contemplated that, in at least some embodiments, the occluding portion 20 has a surface area about 20% larger than the size of orifice 6 of the left atrial appendage 5. In some particular embodiments, the occluding portion 20 of the device 10 can come in one of multiple sizes with the size of the occluding portion 20 selected based, at least in part, on the size of the orifice 6 of the left atrial appendage 5 of a patient. A non-limiting list of possible diameters of the occluding portion 20 includes about 21 mm, about 28 mm, and about 33 mm.

Figure 1B:
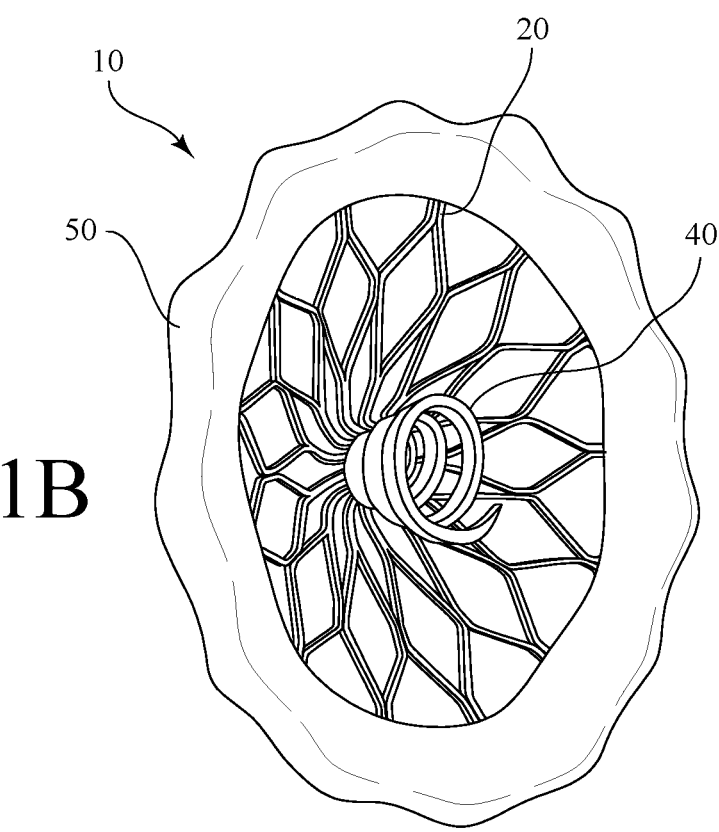
FIG. 1B is a perspective view of the atrial appendage closure device of FIG. 1A and further covered with a membrane.

Referring now to FIGS. 1B and 2B, the occluding portion 20 can, in some embodiments, also be covered by a flexible material or membrane 50 that is supported by the collapsible frame. The membrane 50 is flexible enough to be capable of moving along with the frame of the occluding portion 20 between the retracted position and the deployed position, but the membrane 50 is still sufficiently rigid that the device 10 can provide an effective seal between the left atrial appendage and left atrium of a heart and the membrane 50 will not collapse into the left atrial appendage upon being exposed to the blood flow in the heart and the pressure generated by the left atrium. In some embodiments, the membrane 50 is configured so as to promote epithelialization or, in other words, to promote the deposition of epithelial cells and the growth of an epithelial cell layer over the membrane 50. To this end, it is contemplated that the membrane 50 is generally comprised of a biocompatible material. Biocompatible materials suitable for use in the present invention include, but are not limited to, polytetrafluoroethylene, polyethylene terephthalate or Dacron® (manufactured and supplied by E.I. duPont de Nemours and Co., Inc.). Furthermore, it is contemplated that the biocompatible materials can be provided in a variety of suitable forms including, for example, a velour.

Although not expressly shown in the Figures, the membrane 50 can be connected to the occluding portion 20 by any number of means known in the art including, for example, in some embodiments, an adhesive that is used to bond the membrane 50 to the occluding portion 20. In other embodiments, a physical connection can be utilized, such as, hooks, barbs, clips, wires, or any other such mechanism known in the art. Furthermore, in some embodiments, it is contemplated that an exemplary membrane can be placed over an occluding portion after an atrial appendage closure device of the present invention is implanted. Moreover, an exemplary membrane may be sutured over the occluding portion using the diamond shaped openings in the occluding portion as access points, and the diamond shaped openings in an occluding portion can also be used to suture and thereby secure an atrial appendage closure device of the present invention to the heart of a subject.

To further facilitate the use of the atrial appendage closure device 10, the occluding portion 20 can be coated with an extracellular matrix and/or growth factors using methods known to those of ordinary skill in the art. In some embodiments, the extracellular matrix and/or growth factors are incorporated with the membrane 50 covering the occluding portion 20.

As used herein, the term "growth factor" is used to refer to a substance capable of stimulating cellular growth, proliferation, and cellular differentiation. Such growth factors include, but are not limited to, vascular endothelial growth factor (VEGF), basic fibroblast growth factor (bFGF), insulin-like growth factor (IGF), placental growth factor (PlGF), Ang1, platelet derived growth factor-BB (PDGF-BB), and transforming growth factor β (TGF-β), and combinations thereof. Of course, as would be recognized by those of ordinary skill in the art, various other materials and biological molecules can be attached to or used to coat an atrial appendage closure device of the presently-disclosed subject matter, and can be selected for a particular application as desired.

The term "extracellular matrix" is used herein to refer to the extracellular network of polysaccharides and proteins that typically serve as structural elements to the cells and tissues of a body and that provide a supporting and attachment surface for epithelial cells. In this regard, the term "extracellular matrix" is inclusive of the collection of polysaccharides and proteins that make up the extracellular matrix, but is further used to refer to the individual polysaccharides and proteins that make up the extracellular matrix, as well as the cells, such as fibroblasts and chondrocytes, that contribute to the development of the extracellular matrix. Exemplary polysaccharides and proteins of the extracellular matrix include, but are not limited to: proteoglycans, such as heparin sulfate, chondroitin sulfate, and keratin sulfate; non-proteoglycan polysaccharides, such as hyaluronic acid; collagen; elastin; fibronectin; and laminin.

By including an extracellular matrix, the device 10 can be configured so as to promote epithelialization or, in other words, to promote the deposition of epithelial cells and the growth of an epithelial cell layer over the surface of the device 10. In this regard, by promoting epithelialization over the device 10, the device 10 is kept from being directly exposed to the circulating blood within the heart of a subject and scar tissue formation, immune reactions, or any other adverse events commonly associated with the implantation of a foreign body into a living subject are thereby minimized or prevented. In some embodiments, the distal surface 22 of an exemplary occluding portion 20, or the membrane 50 covering the distal surface 22 of the occluding portion 20, is coated with an extracellular matrix, growth factors, or both to promote epithelialization or the formation of an epithelial cell layer over the entire surface of the occluding portion 20 that is placed into direct contact with the left atrium 4 of the heart 1. Of course, it is also contemplated that the proximal surface 24 of an exemplary occluding portion 20 or any other portion of an exemplary atrial appendage closure device 10, can also be coated with an extracellular matrix or with growth factors without departing from the spirit and scope of the subject matter described herein. For example, it is contemplated that the anchoring portion 40 of the device 10 can be coated with an extracellular matrix such that, upon insertion of the device 10, there is no area of the device 10 where cells are not able to adhere or where a hole may be created between the device 10 and the surrounding tissue, which may then lead to blood stasis and blood clot formation.

Figure 5:
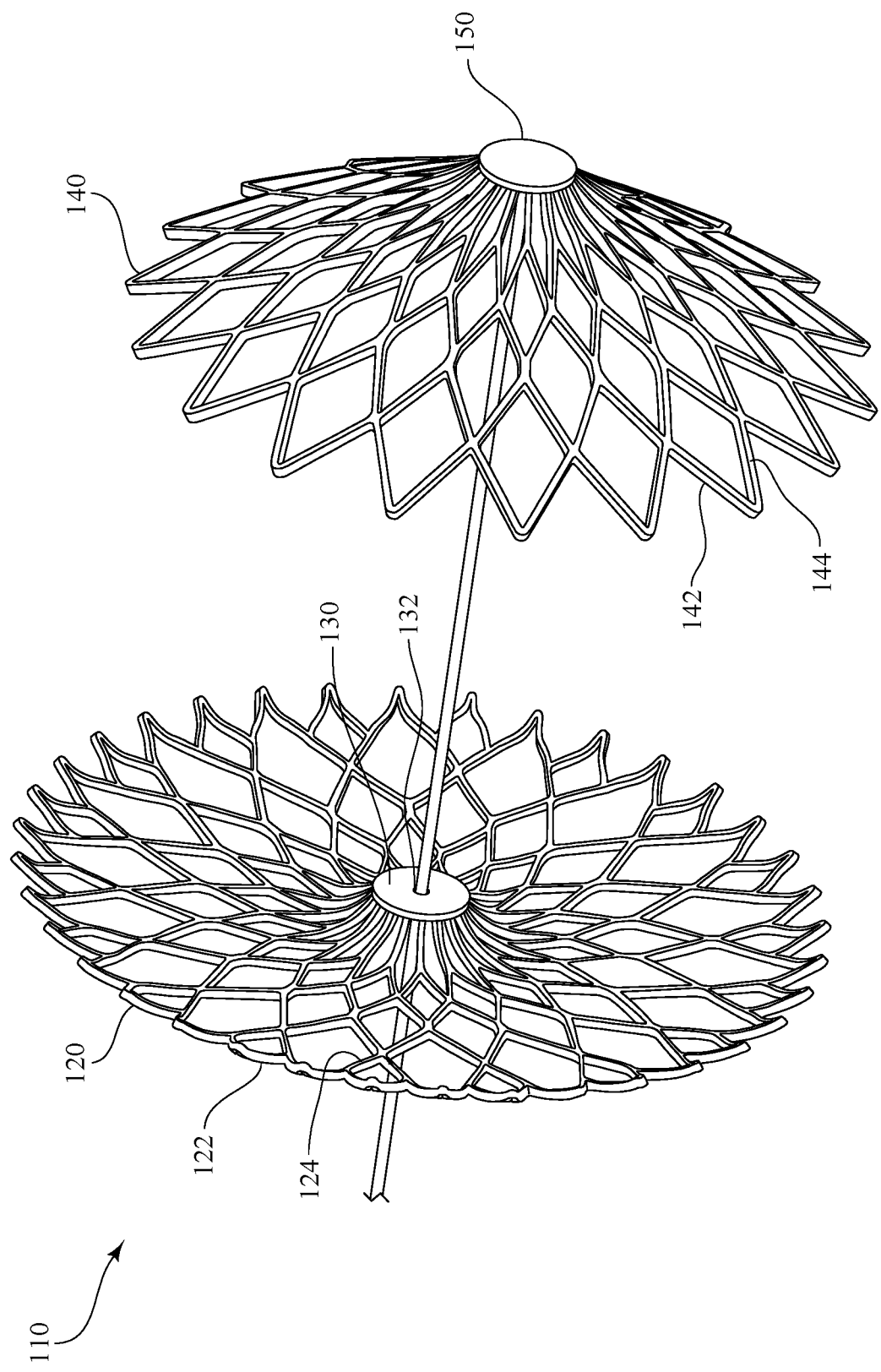
FIG. 5 is a perspective view of another exemplary atrial appendage closure device made in accordance with the present invention and including an occluding portion in a deployed position and an anchoring portion in a deployed position.
Figure 6:
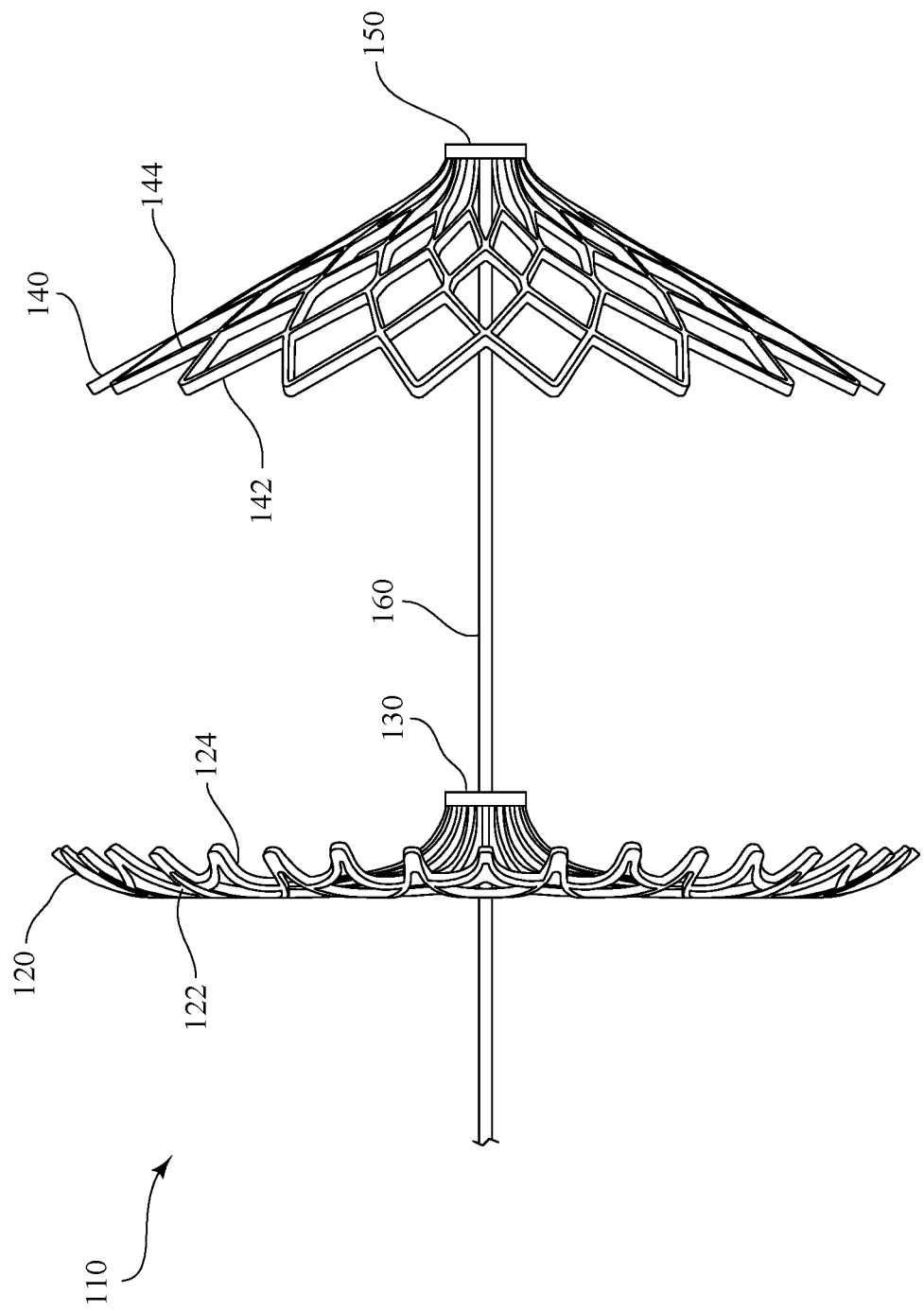
FIG. 6 is a side view of the atrial appendage closure device of FIG. 5.
Figure 7:
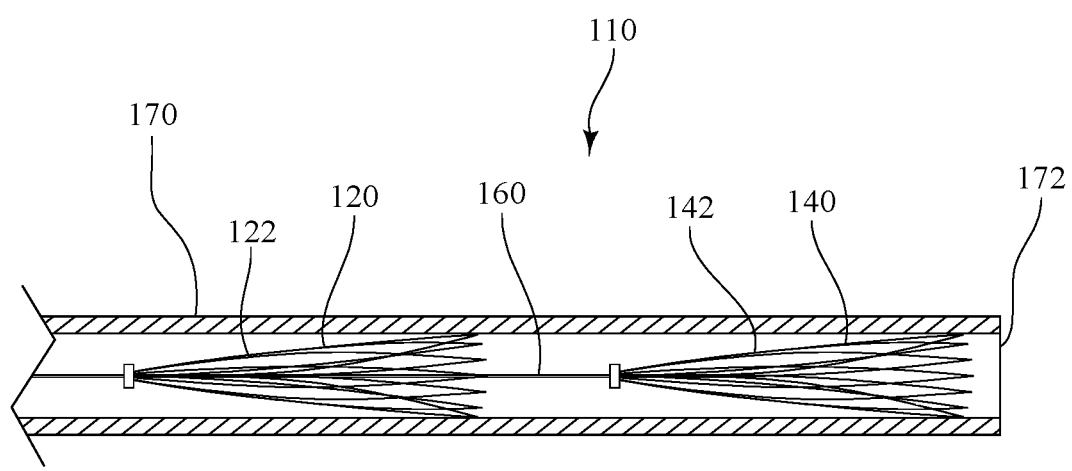
FIG. 7 is a side view of the atrial appendage closure device of FIG. 5 positioned within a delivery catheter and with the occluding portion schematically represented in a forward facing retracted position and the anchoring portion schematically represented in a forward facing retracted position.

Referring now to FIGS. 5-7, in another exemplary embodiment of the present invention, instead of having an anchoring portion shaped like a corkscrew connected to the occluding portion, an atrial appendage closure device 110 made in accordance with the present invention includes an occluding portion 120 and an anchoring portion 140 that are both comprised of a collapsible frame in a starburst pattern. Of note, the starburst pattern shown in FIG. 5 includes substantially more curved tips than the starburst pattern previously described. The configuration of the collapsible frames of the present invention, however, is not limited and can include a variety of different configurations and patterns other than or in addition to the starburst patterns shown in the exemplary embodiments described and shown herein without departing from the spirit and scope of the present invention.

Similar to the occluding portion 20 described above, in the embodiment shown in FIGS. 5-7, the occluding portion 120 has a distal surface 122 and a proximal surface 124 opposite the distal surface 122. In this embodiment, the anchoring portion 140 also has a distal surface 144 and a proximal surface 142 opposite the distal surface 144, with the proximal surface 142 of the anchoring portion 140 facing the proximal surface 124 of the occluding portion 120. As also shown in FIGS. 5-7, the anchoring portion 140 has a hub 150 with a deployment member 160 that is connected to the hub 150 of the anchoring portion 140 on the proximal surface side of the anchoring portion 140. Furthermore, the occluding portion 120 has a hub 130 defining a hole 132 and the deployment member 160, in the form of a wire, extends away from the anchoring portion 140 and through the hole 132 of the occluding portion 120, as further discussed below. Of course, while the deployment member 160 is in the form of a wire in this particular embodiment, it is nonetheless contemplated that in other embodiments the deployment member can be in the form of a rod or other similar element capable of maintaining tension when pulled, as also further discussed below.

In this embodiment, both the occluding portion 120 and the anchoring portion 140 are movable between a retracted position and a deployed position. As shown in FIGS. 5-6, when the occluding portion 120 is in the deployed position, it extends outward to form a substantially flat disc, like the occluding portion 20 described above with reference to FIGS. 1-2, but when the anchoring portion 140 is in the deployed position, it assumes an umbrella-like shape with the proximal surface 142 of the anchoring portion 40 assuming a concave shape and the distal surface 144 of the anchoring portion 140 assuming a convex shape.

Referring now specifically to FIG. 7 which shows the device 110 positioned within a catheter 170, when the occluding portion 120 is in the retracted position, the occluding portion 120 is collapsed towards the anchoring portion 140, but when the anchoring portion 140 is in the retracted position, the anchoring portion 140 is collapsed away from the occluding portion 120. In other words, both the occluding portion 120 and the anchoring portion 140 face towards the open end 172 of the delivery catheter 170. It should be noted that in moving from the retracted position to the deployed position, the anchoring portion 140 opens about 120° in the direction of the proximal surface 142 of the anchoring portion 140 whereas the occluding portion 120 opens about 90° in the direction of the distal surface 122 of the occluding portion 120.

Although not shown in FIGS. 5-7, it is contemplated that the occluding portion 120, the anchoring portion 140, or both can also be covered by a flexible material or membrane similar to the membrane 50 described above with reference to FIGS. 1A and 1B. Similarly, the occluding portion 120, the anchoring portion 140, or both can also be coated with an extracellular matrix and growth factors using methods known to those of ordinary skill in the art.

Referring now to FIGS. 8A-8H, in another exemplary implementation of the method of occluding a left atrial appendage of a heart of the present invention, an atrial appendage closure device 110 is first provided and positioned within a catheter 170 with the occluding portion 120 and the anchoring portion 140 both in a retracted position, as shown in FIG. 7.

Figure 8A:
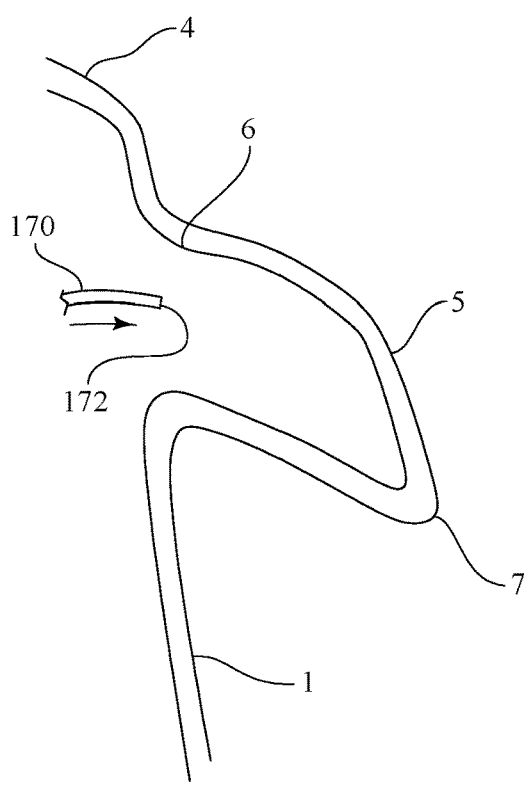
FIGS. 8A-8H are a series of schematic representations of another exemplary method of occluding a left atrial appendage in accordance with the presently-disclosed subject matter, in which the atrial appendage closure device of FIG. 5 is deployed to provide a seal between the left atrial appendage and the left atrium of a heart.

Next, as shown in FIG. 8A, the atrial appendage closure device 110 is implanted using a transseptal approach via the femoral vein of a subject using an over the guidewire, modified Seldinger's technique until the catheter 170 is positioned within the left atrium 4 adjacent to the left atrial appendage 5 with the end 172 of the catheter 170 positioned within the orifice 6 of the left atrial appendage 5.

Figure 8B:
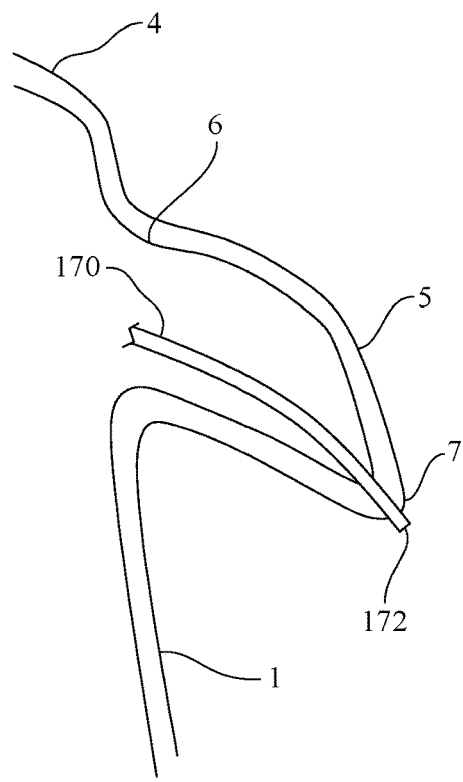
Figure 8C:
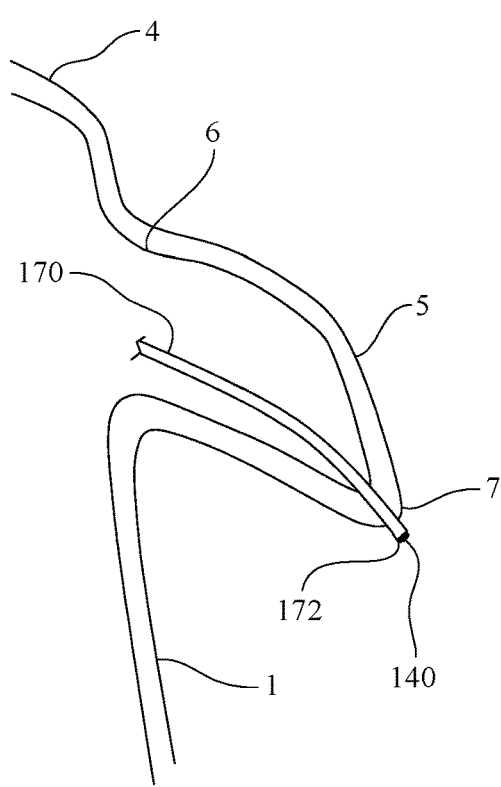
Figure 8D:
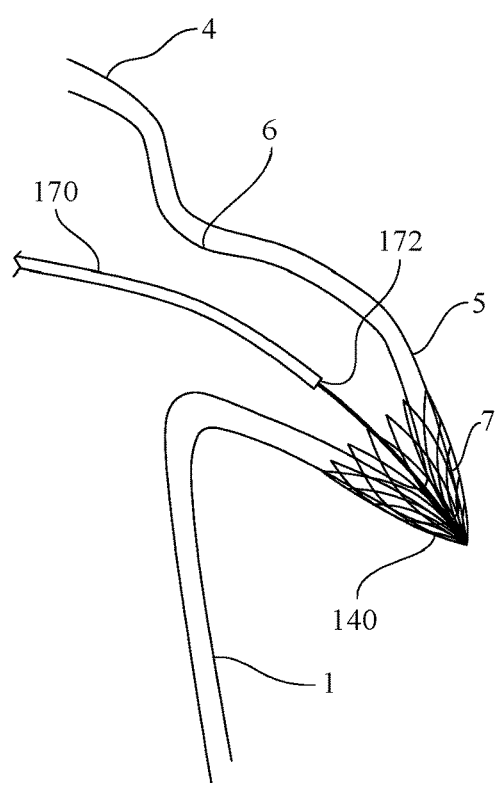

Referring now to FIG. 8B, the catheter 170 is extended into the left atrial appendage 5 and through the wall of the left atrial appendage 5 near the apex 7 of the left atrial appendage 5 until the end 172 of the catheter 170 is positioned entirely outside of the heart 1.

Referring now to FIGS. 8C-8F, after the end 172 of the catheter 170 is positioned outside of the heart 1, the atrial appendage closure device 110 is extended forward out of the catheter 170, unsheathing the anchoring portion 140 and allowing the anchoring portion 140 to deploy outside of the heart 1 adjacent to the apex 7 of the left atrial appendage 5. The catheter 170, with the occluding portion 120 still contained within, is then drawn backward into the left atrial appendage. As previously mentioned, the deployment member 160 is connected to the hub 150 of the anchoring portion 140 and extends through a hole 132 defined through a hub 130 of the occluding portion 120. As such, the catheter 170 with the occluding portion 120 of the atrial appendage closure device 110 still contained within is able to be drawn backward into the left atrium 4 without pulling on the deployment member 160, leaving a length of the deployment member 160 left exposed extending out from the catheter 170 to the anchoring portion 140 positioned outside of the heart 1.

Figure 8E:
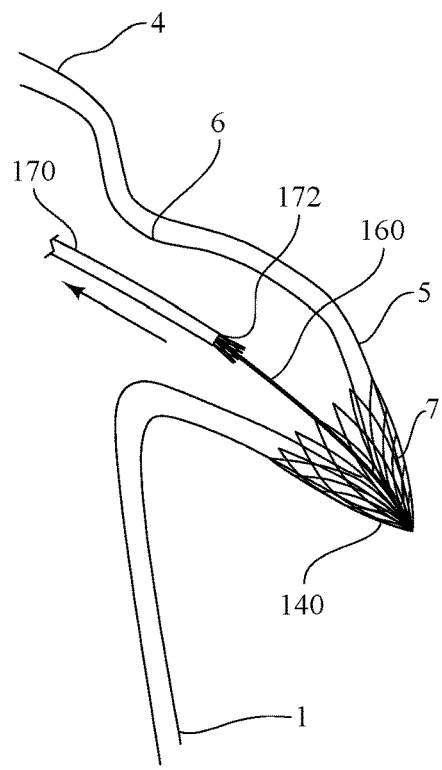
Figure 8F:
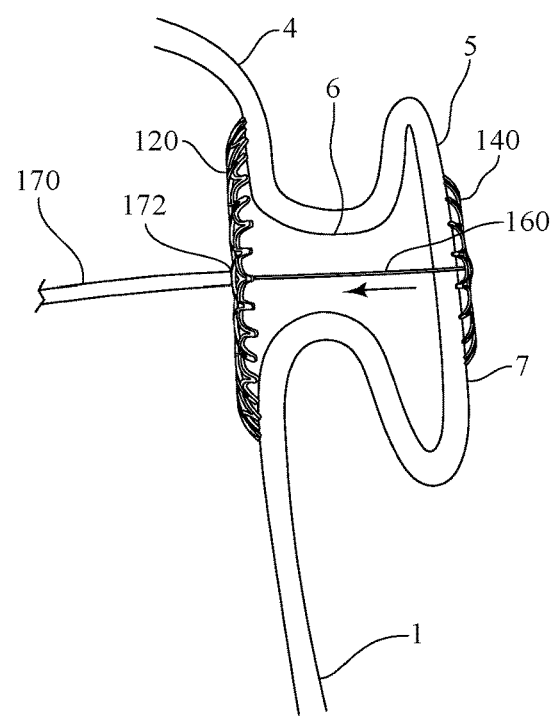

Referring now to more particularly to FIGS. 8E-8F, after the catheter 170 is positioned entirely within the left atrium 4, the occluding portion 120 of the device 110 is removed from the catheter 170 allowing the occluding portion 120 to deploy inside the left atrium 4 and form a seal across the orifice 6 of the left atrial appendage 5.

Figure 8G:
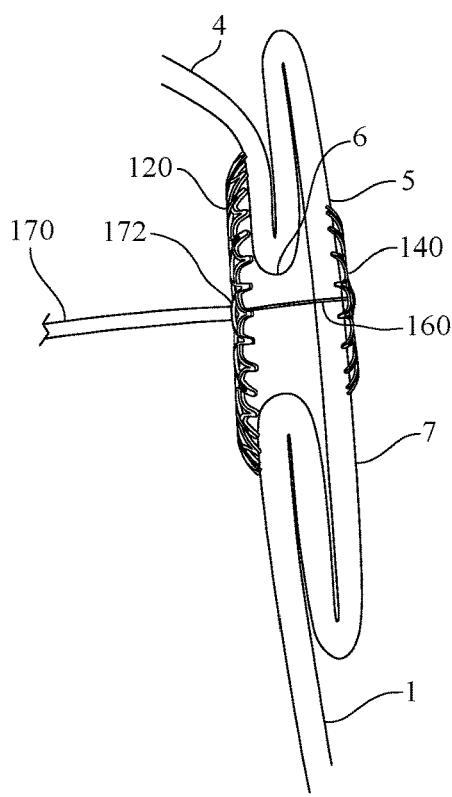
Figure 8H:
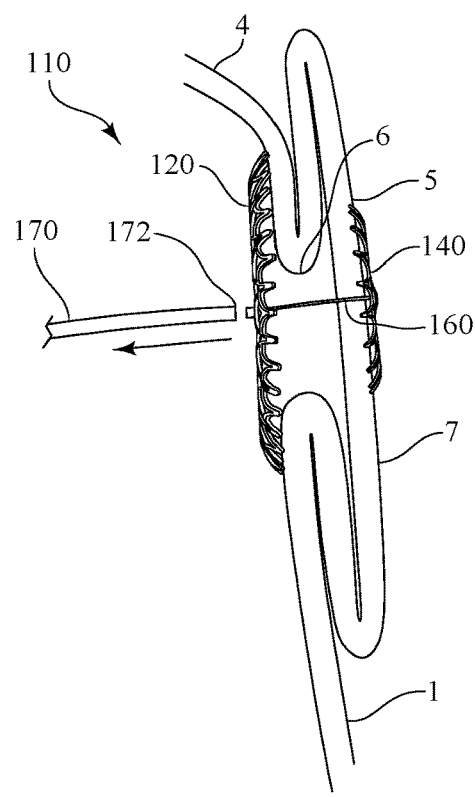

Referring now to FIGS. 8G-8H, the deployment member 160 is drawn back into the catheter 170 pulling the anchoring portion 140 towards the occluding portion 120 until the apex 7 of the left atrial appendage 5 is positioned adjacent to the orifice 6 of the left atrial appendage 5 and the left atrial appendage 5 is completely collapsed. As the anchoring portion 140 is pulled towards the occluding portion 120, the anchoring portion 140 continues to open into a substantially flat disc, similar to the occluding portion 120 except smaller. Of course, the relative sizes of the occluding portion and the anchoring portion can be modified according to the particular needs, anatomy of the subject, and application of the occluding device without departing from the spirit and scope of the present invention.

Although in the exemplary implementation shown in FIG. 8G the anchoring portion 140 is pulled towards the occluding portion 120 until the left atrial appendage 5 is completely collapsed, it should be understood that the distance between the anchoring portion 140 and the occluding portion 120 is fully adjustable such that any degree of compression of the left atrial appendage 5, including no compression, is also possible without departing from the spirit and scope of the present invention.

As shown in FIG. 8H, the occluding portion 120 is then secured to the anchoring portion 140, for example, by affixing a portion of the deployment member 160 to the hub 130 of the occluding portion 120, and the catheter 170 is withdrawn, leaving the device 110 implanted in the heart 1.

Referring now to FIGS. 9A-9H, in another exemplary implementation of the method of occluding a left atrial appendage of a heart of the present invention, the anchoring portion is deployed outside of the heart at a portion of the left atrial appendage other than the apex. Like the method described above with reference to FIGS. 8A-8H, an atrial appendage closure device 110 is first provided and positioned within a catheter 170 with the occluding portion 120 and the anchoring portion 140 both in a retracted position, as shown in FIG. 7.

Figure 9A:
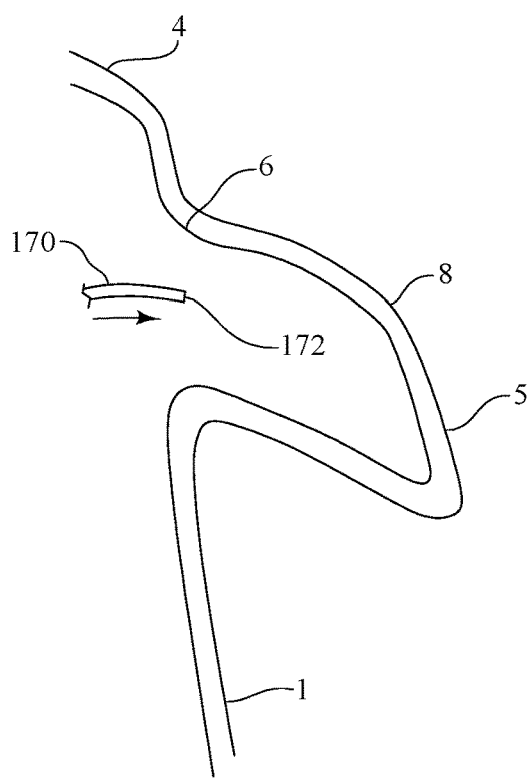
FIGS. 9A-9H are a series of schematic representations of another exemplary method of occluding a left atrial appendage in accordance with the presently-disclosed subject matter, in which the atrial appendage closure device of FIG. 5 is deployed to provide a seal between the left atrial appendage and the left atrium of a heart.

Next, as shown in FIG. 9A, the atrial appendage closure device 110 is implanted using a transseptal approach via the femoral vein of a subject using an over the guidewire, modified Seldinger's technique until the catheter 170 is positioned within the left atrium 4 adjacent to the left atrial appendage 5 with the end 172 of the catheter 170 positioned within the orifice 6 of the left atrial appendage 5.

Figure 9B:
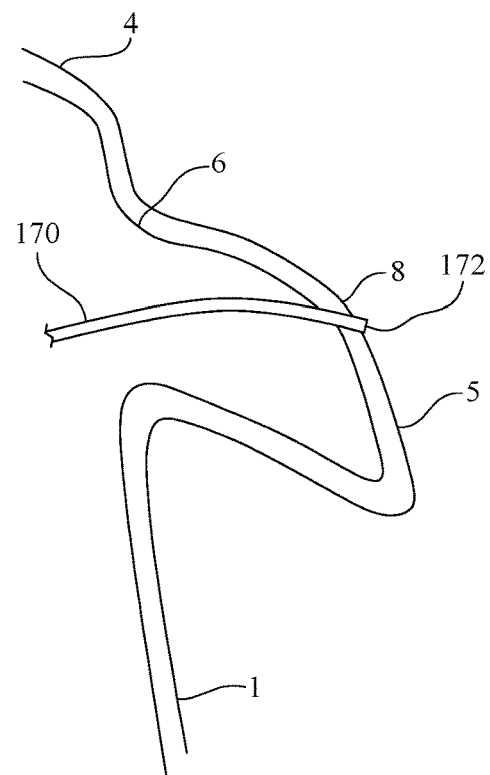

Referring now to FIG. 9B, the catheter 170 is extended into the left atrial appendage 5 and through a remote wall 8 of the left atrial appendage 5 positioned away from the orifice 6 of the left atrial appendage 5 until the end 172 of the catheter 170 is positioned entirely outside of the heart 1.

Figure 9C:
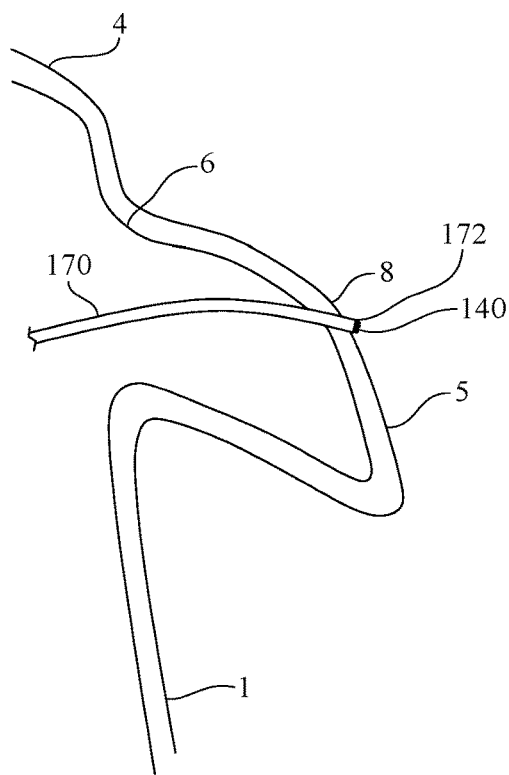
Figure 9D:
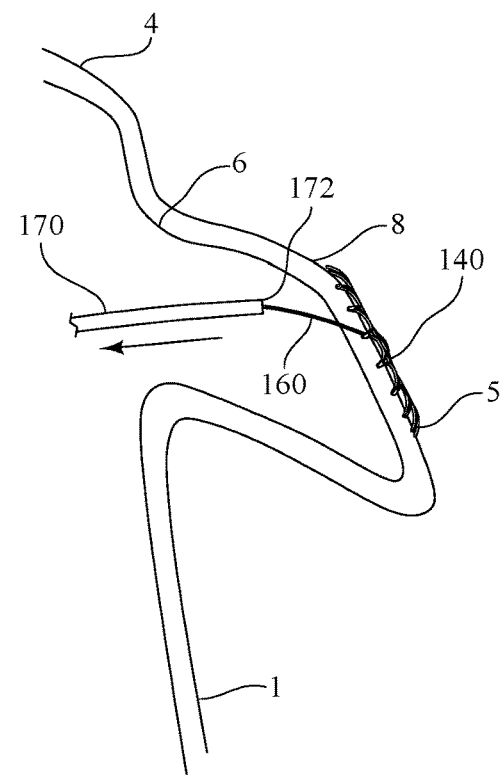

Referring now to FIGS. 9C-9D, after the end 172 of the catheter 170 is positioned outside of the heart 1, the atrial appendage closure device 110 is extended forward out of the catheter 170, unsheathing the anchoring portion 140 and causing the anchoring portion 140 to deploy outside of the heart 1. As shown in FIG. 9D, the catheter 170, with the occluding portion 120 still contained within, is then drawn backward into the left atrial appendage 5. Once again, a length of the deployment member 160 is left exposed extending out from the catheter 170 to the anchoring portion 140 positioned outside of the heart 1.

Figure 9E:
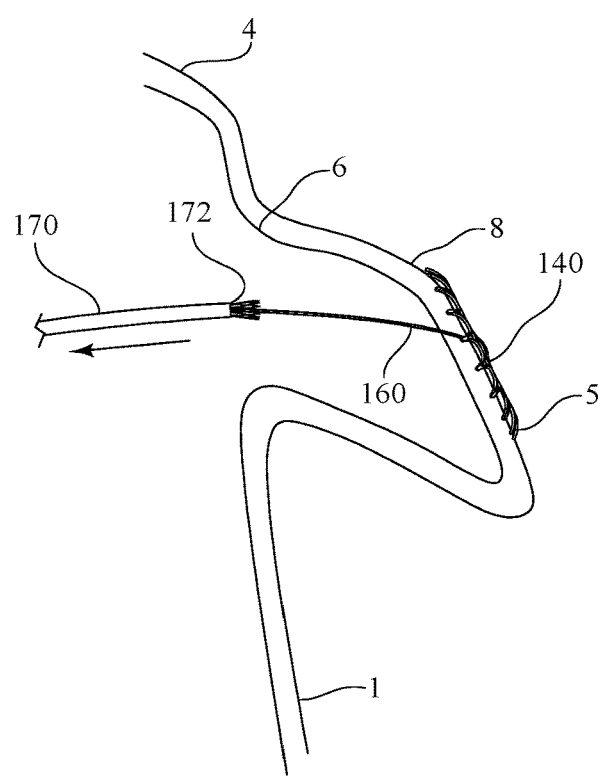
Figure 9F:
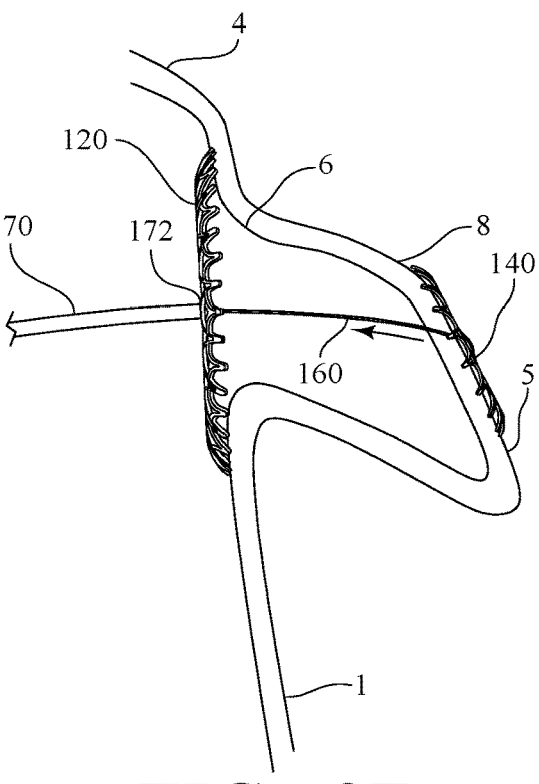

Referring now to FIGS. 9E-9F, after the catheter 170 is positioned entirely within the left atrium 4, the occluding portion 120 of the device 110 is removed from the catheter 170 allowing the occluding portion 120 to deploy inside the left atrium 4 and form a seal across the orifice 6 of the left atrial appendage 5.

Figure 9G:
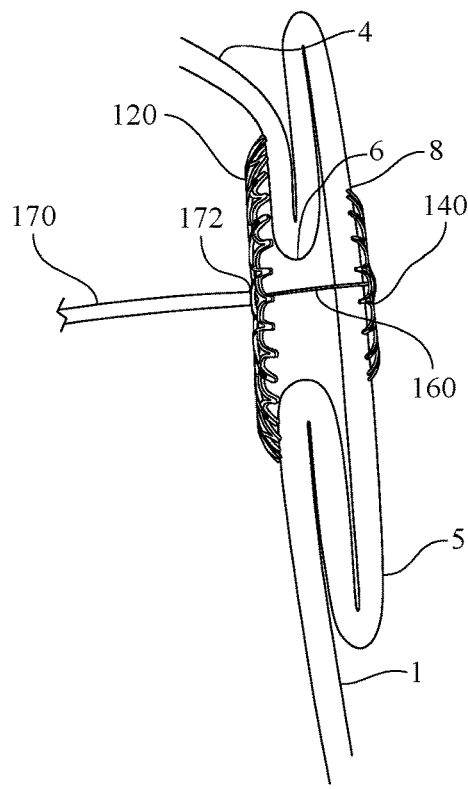
Figure 9H:
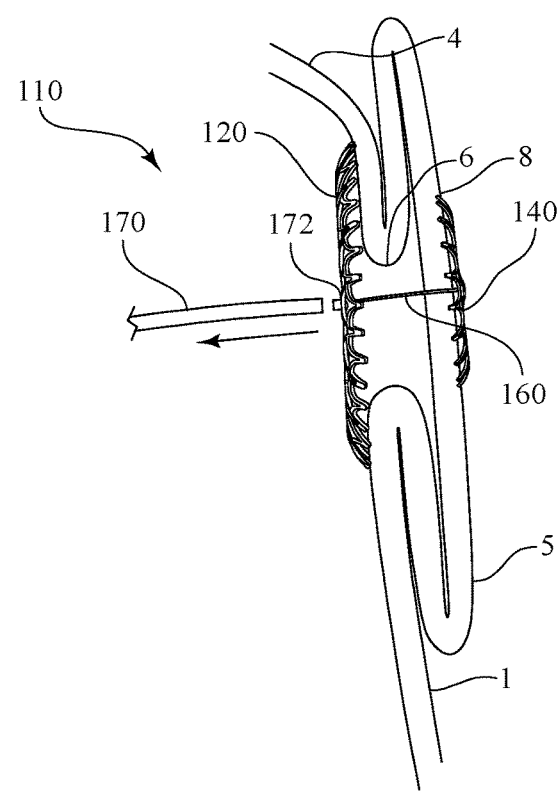

Referring now to FIGS. 9G-9H, the deployment member 160 is drawn back into the catheter 170, pulling together the anchoring portion 140 and the occluding portion 120 until the remote wall 8 of the left atrial appendage 5 is positioned adjacent to the orifice 6 of the left atrial appendage 5 and the left atrial appendage 5 is completely collapsed. Once again, it should be understood that the distance between the anchoring portion 140 and the occluding portion 120 is fully adjustable such that any degree of compression of the left atrial appendage 5 is possible, including no compression, without departing from the spirit and scope of the present invention. As shown in FIG. 9H, after securing the occluding portion 120 to the anchoring portion 140, the catheter 170 is withdrawn, leaving the device 110 implanted in the heart 1.

FIGS. 10A-10H depict another exemplary implementation of the method of occluding a left atrial appendage 5 of a heart 1 of the present invention substantially the same as the method shown in FIGS. 9A-9H except that, the anchoring portion 240 of the exemplary atrial appendage closure device 210 shown in FIGS. 10A-10H further includes a plurality of barbs that latch onto the exterior wall of the left atrial appendage 5, keeping the anchoring portion 240 secured in place.

Figure 10A:
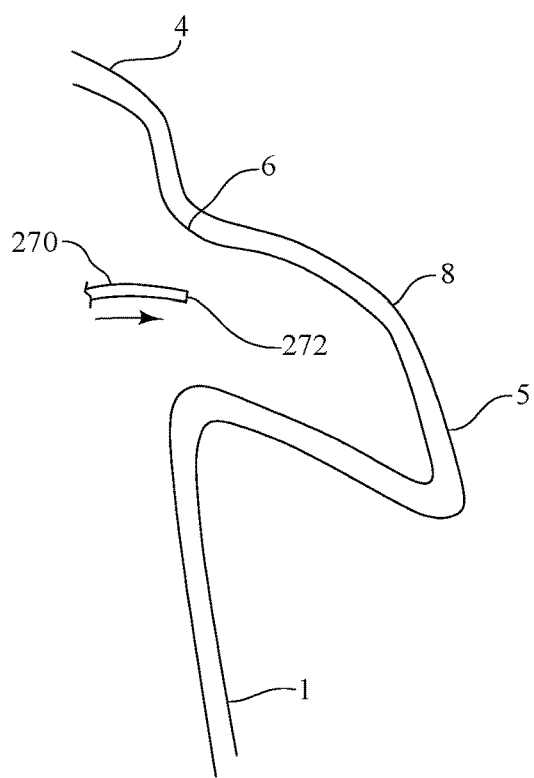
FIGS. 10A-10H are a series of schematic representations of an exemplary method of occluding a left atrial appendage in accordance with the presently-disclosed subject matter, in which another atrial appendance closure device similar to the atrial appendage closure device of FIG. 5, but further including barbs, is deployed to provide a seal between the left atrial appendage and the left atrium of a heart.
Figure 10B:
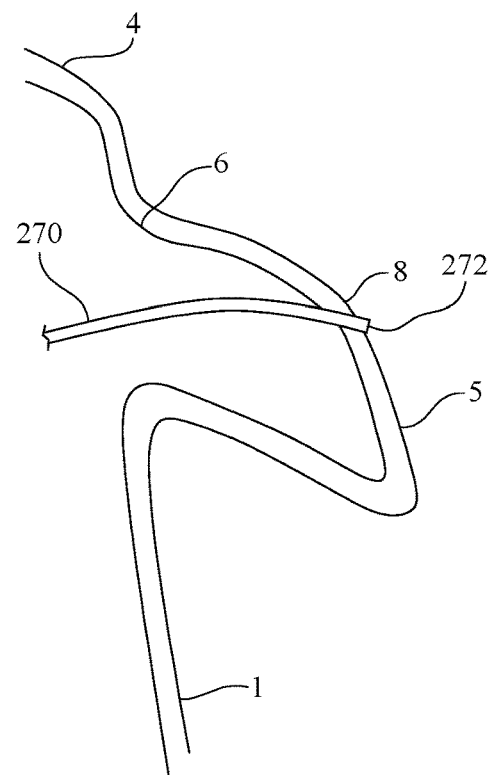
Figure 10C:
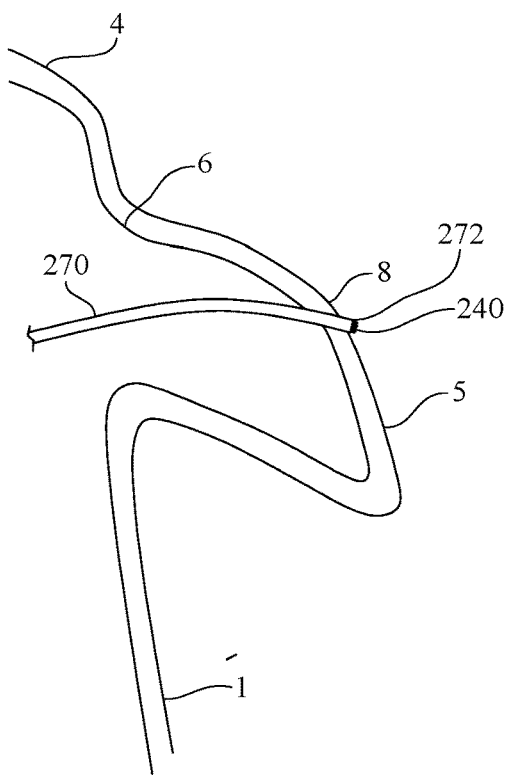
Figure 10D:
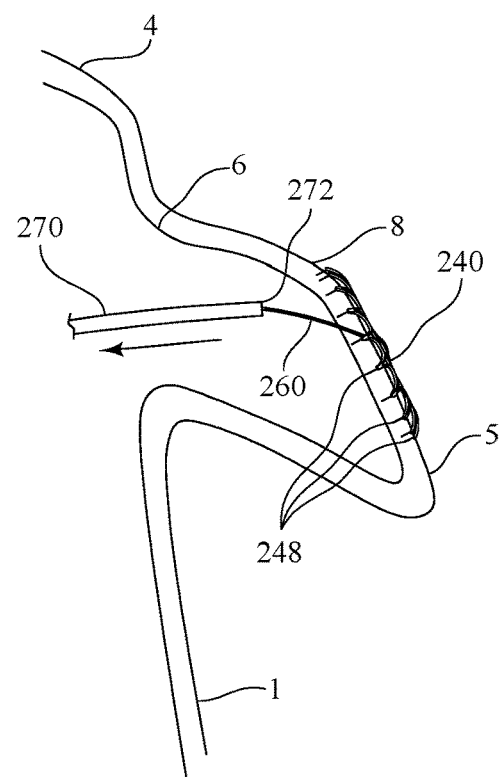
Figure 10E:
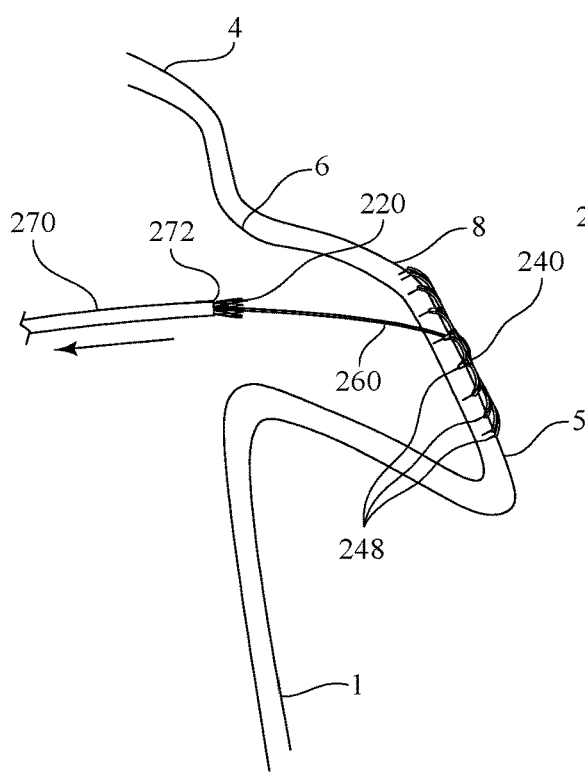
Figure 10F:
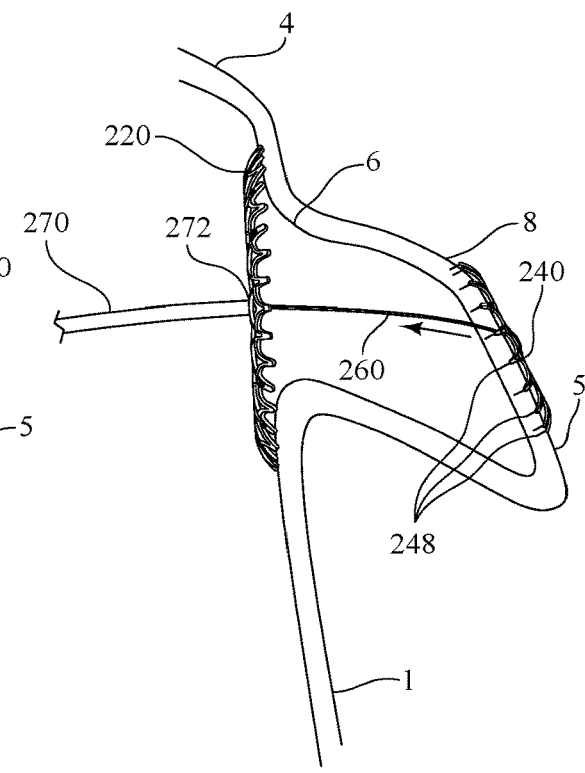
Figure 10G:
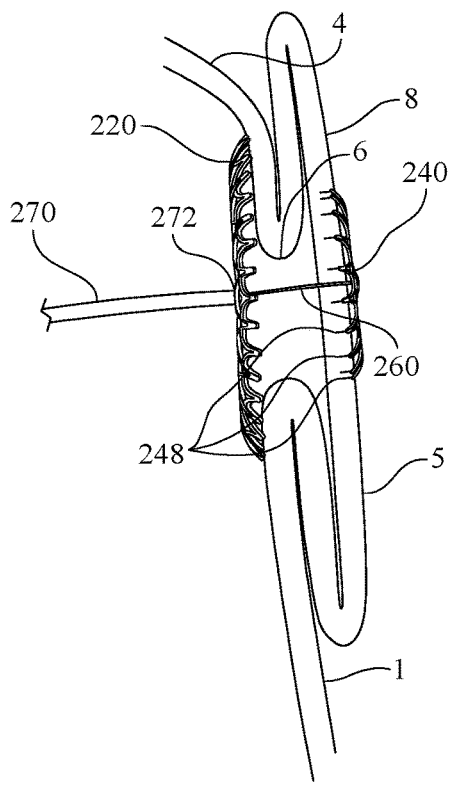
Figure 10H:
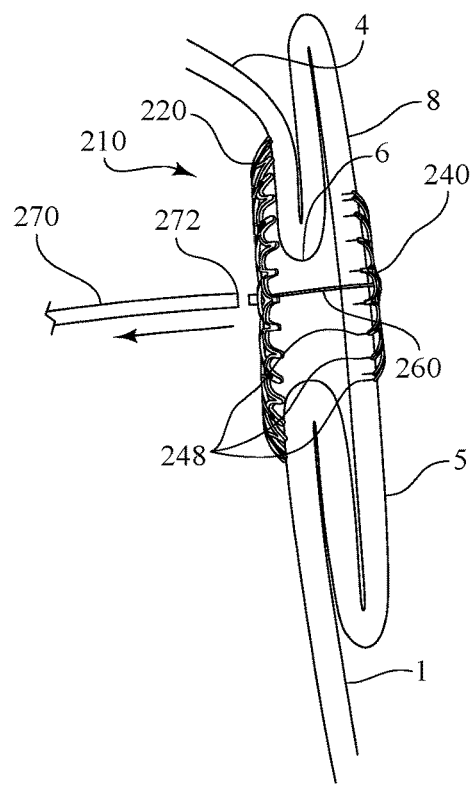

Specifically, as shown in FIGS. 10A-10D, the catheter 270 is extended through a remote wall 8 of the left atrial appendage 5 and the anchoring portion 240 is deployed in substantially the same manner as shown in FIGS. 9A-9D. However, as shown in FIG. 10D, when the anchoring portion 240 is deployed outside of the heart 1, a plurality of barbs 248 pierce into the exterior wall of the left atrial appendage 5, keeping the anchoring portion 240 secured in place. To this end, in this exemplary embodiment, the barbs 248 extend away from the proximal surface 242 of the anchoring portion 240, but other configurations are also contemplated.

The remaining steps shown in FIGS. 10E-10H are substantially identical to the method steps shown in FIGS. 9E-9H. Specifically, the occluding portion 120 is deployed inside the left atrium 4 (FIGS. 10E-10F), the anchoring portion 140 and the occluding portion 220 are pulled together by the deployment member 260 (FIG. 10G), and the occluding portion 220 is secured to the anchoring portion 240 (FIG. 10H), leaving the device 210 implanted in the heart 1 with the left atrial appendage 5 collapsed.

Figure 11:
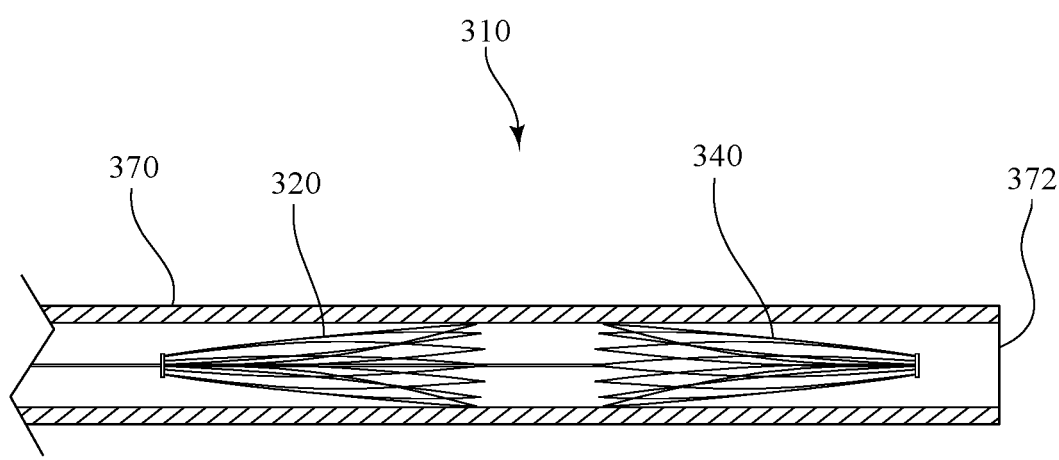
FIG. 11 is a side view of another exemplary atrial appendage closure device made in accordance with the present invention and positioned within a delivery catheter with the occluding portion schematically represented in a forward facing retracted position and the anchoring portion schematically represented in a rearward facing retracted position.

Referring now to FIG. 11, in another exemplary embodiment of the present invention, an atrial appendage closure device 310 made in accordance with the present-disclosed subject matter includes an occluding portion 320 and an anchoring portion 340 that are both comprised of a collapsible frame in a starburst pattern, substantially the same as the device 110 described above with respect to FIGS. 5-7 except that when the anchoring portion 340 is in the retracted position within the catheter 370, the anchoring portion 340 is collapsed toward the occluding portion 320 rather than away from the occluding portion 320. In other words, both the occluding portion 320 and the anchoring portion 340 are collapsed towards each other. Furthermore, as shown in FIGS. 12D-12H, the anchoring portion 340 further includes a plurality of barbs 348 extending away from the distal surface 346 of the anchoring portion 340 which help secure the anchoring portion 340 within the left atrial appendage 5, as further discussed below.

Referring now to FIGS. 12A-12H, in another exemplary implementation of the method of occluding a left atrial appendage of a heart of the present invention, the anchoring portion is deployed within the left atrial appendage rather than outside of the heart. An atrial appendage closure device 310 is first provided and positioned within a catheter 370 with the occluding portion 320 and the anchoring portion 340 both in a retracted position, as shown in FIG. 11.

Figure 12A:
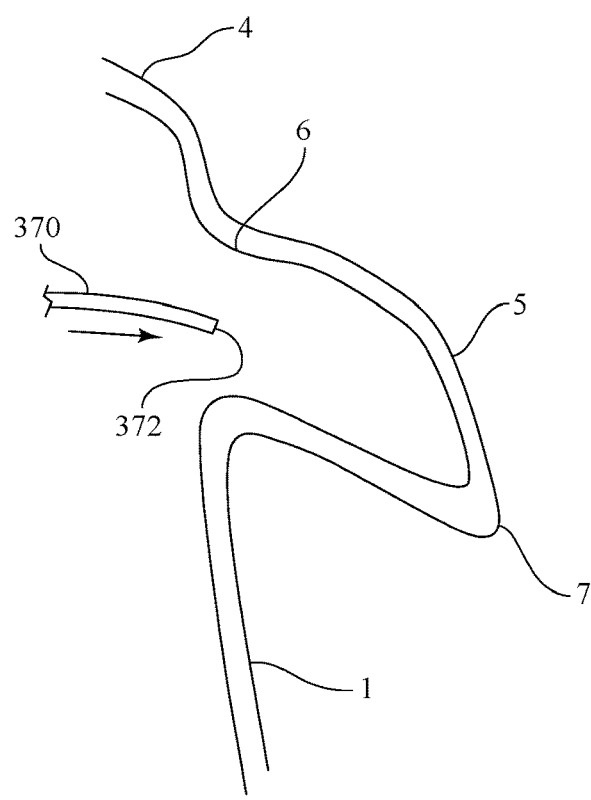
FIGS. 12A-12H are a series of schematic representations of another exemplary method of occluding a left atrial appendage in accordance with the presently-disclosed subject matter, in which the atrial appendage closure device of FIG. 11 is deployed to provide a seal between the left atrial appendage and the left atrium of a heart.
Figure 12B:
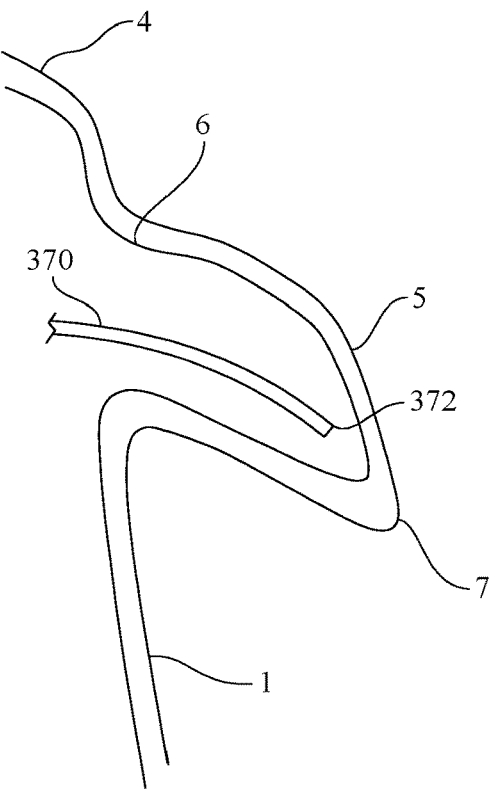

Referring now to FIGS. 12A-12B, the catheter 370 is then positioned within the left atrial appendage 5 with the end 372 of the catheter 370 positioned adjacent to the apex 7 of the left atrial appendage 5.

Figure 12C:
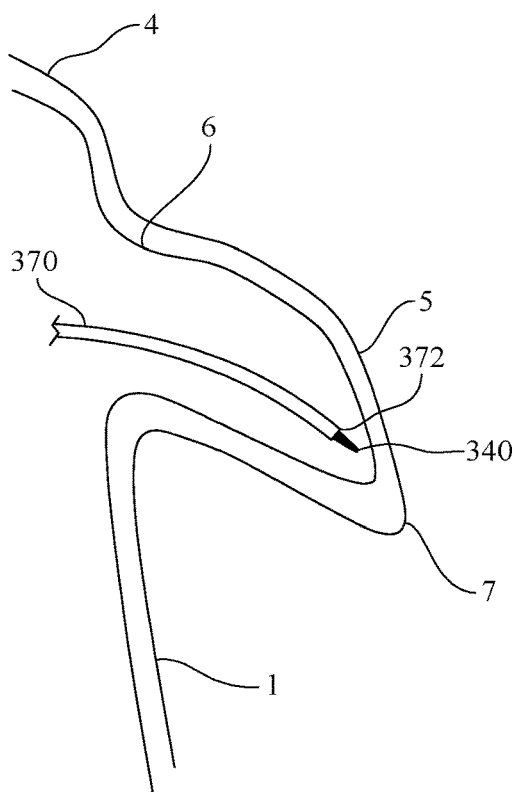
Figure 12D:
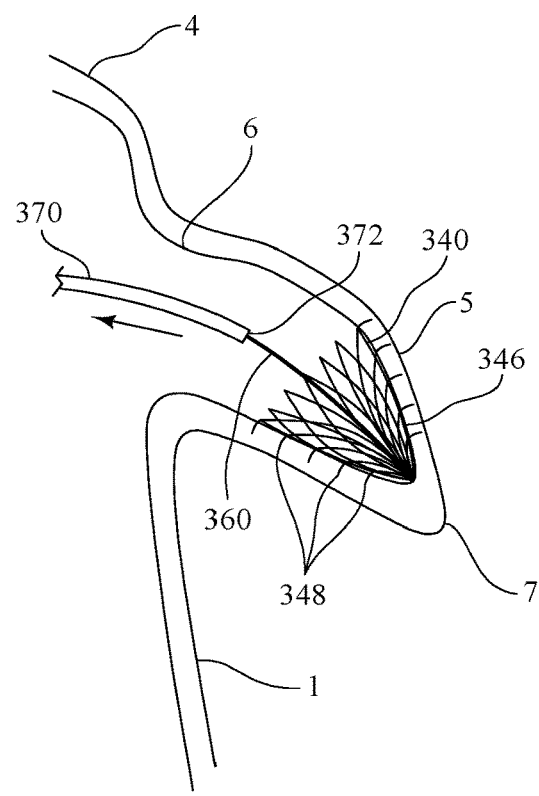

Referring now to FIGS. 12C-12D, the atrial appendage closure device 310 is extended forward out of the catheter 370, unsheathing the anchoring portion 340 and allowing the anchoring portion 340 to deploy. As a result of the orientation of the anchoring portion 340 in the retracted position (i.e., collapsed towards the occluding portion 320) when the anchoring portion 340 deploys from the retracted position to the deployed position, the anchoring portion 340 opens less than 90° in the direction of the distal surface 346 of the anchoring portion 340 such that it assumes an umbrella-like shape within the left atrial appendage 5. As shown in FIG. 12D, when the anchoring portion 340 is deployed within the left atrial appendage 5, the plurality of barbs 348 extending away from the distal surface 346 of the anchoring portion 340 pierce into the interior wall of the left atrial appendage 5, keeping the anchoring portion 340 secured in place. To this end, it is contemplated that in the retracted position the anchoring portion 340 has sufficient stored energy such that, when deployed, the anchoring portion 340 can force the barbs 348 into the interior wall of the left atrial appendage 5.

Figure 12E:
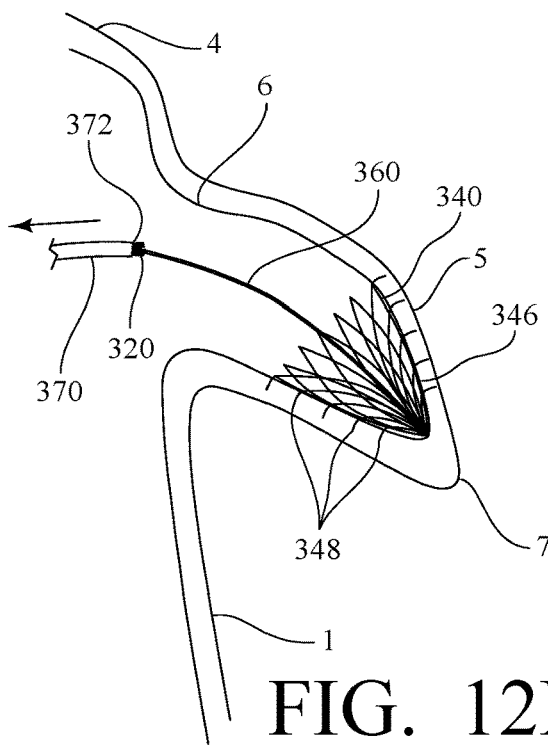
Figure 12F:
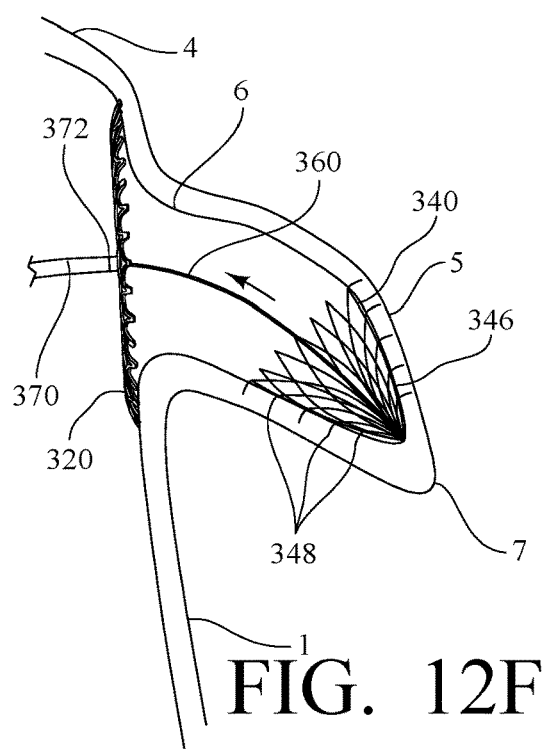

Referring now to FIGS. 12E-12F, the catheter 370, with the occluding portion 320 still contained within, is then drawn backward into the left atrium 4 leaving a length of the deployment member 360 exposed extending out from the catheter 370 to the anchoring portion 340, substantially the same as described above. As shown in FIG. 12F, after the catheter 370 is positioned entirely within the left atrium 4, the occluding portion 320 of the device 310 is removed from the catheter 370 allowing the occluding portion 320 to deploy inside the left atrium 4 and form a seal across the orifice 6 of the left atrial appendage 5.

Figure 12G:
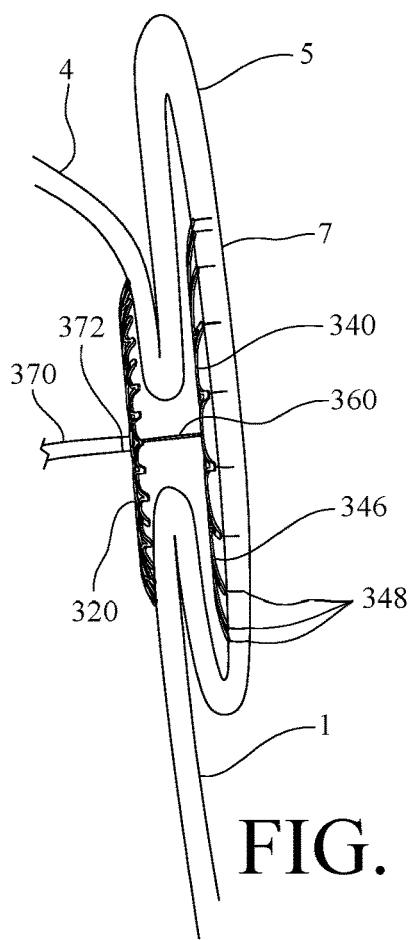

Referring now to FIG. 12G, the deployment member 360 is drawn back into the catheter 370 pulling the anchoring portion 340 towards the occluding portion 320 until the apex 7 of the left atrial appendage 5 is positioned adjacent to the orifice 6 of the left atrial appendage 5 and the left atrial appendage 5 is completely collapsed. As the anchoring portion 340 is pulled towards the occluding portion 320, the anchoring portion 340 continues to open from the umbrella-like shape into a substantially flat disc, similar to the occluding portion 320. In doing so, the anchoring portion 340 also pushes the sides the left atrial appendage 5 outward causing the left atrial appendage 5 to completely collapse. Once again, it should be understood that the distance between the anchoring portion 340 and the occluding portion 320 is fully adjustable such that any degree of compression of the left atrial appendage 5 is possible.

Figure 12H:
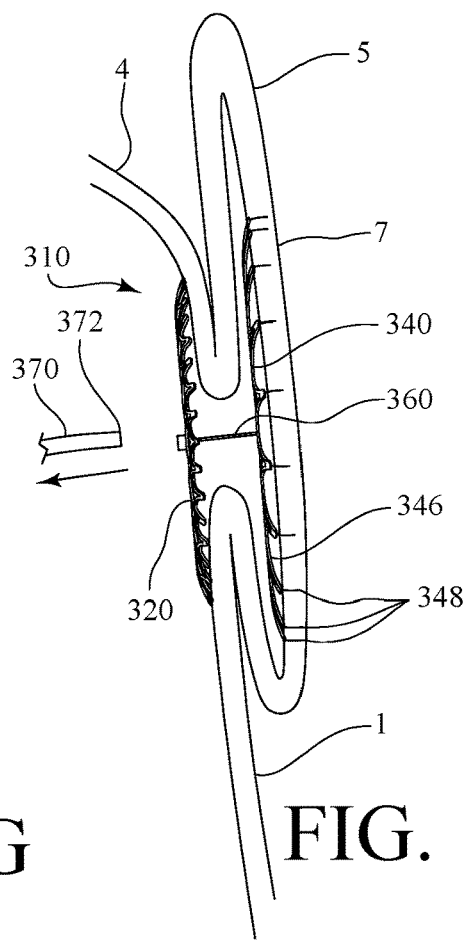

As shown in FIG. 12H, the occluding portion 320 is then secured to the anchoring portion 340, for example, by affixing a portion of the deployment member 360 to the hub 330 of the occluding portion 320, and the catheter 370 is withdrawn, leaving the device 310 implanted in the heart 1.

Figure 13A:
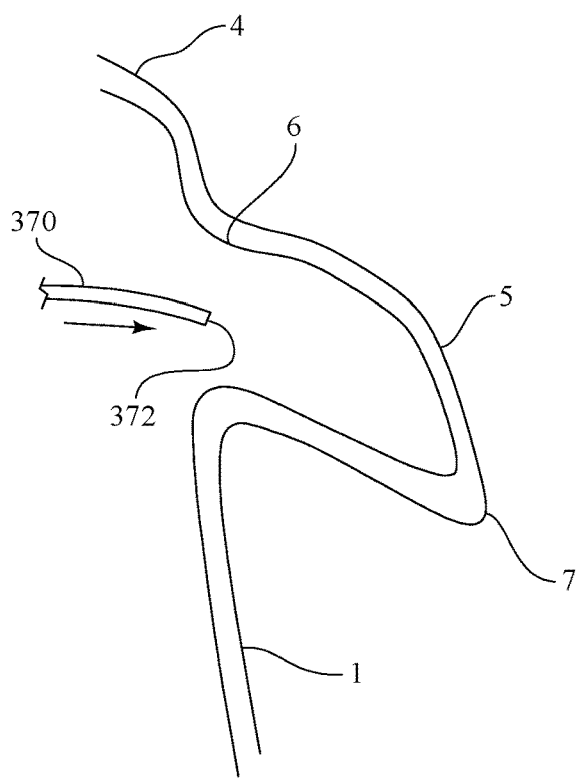
FIGS. 13A-13H are a series of schematic representations of another exemplary method of occluding a left atrial appendage in accordance with the presently-disclosed subject matter, in which another atrial appendage closure device similar to the atrial appendage closure device of FIG. 11 is deployed to provide a seal between the left atrial appendage and the left atrium of a heart.
Figure 13B:
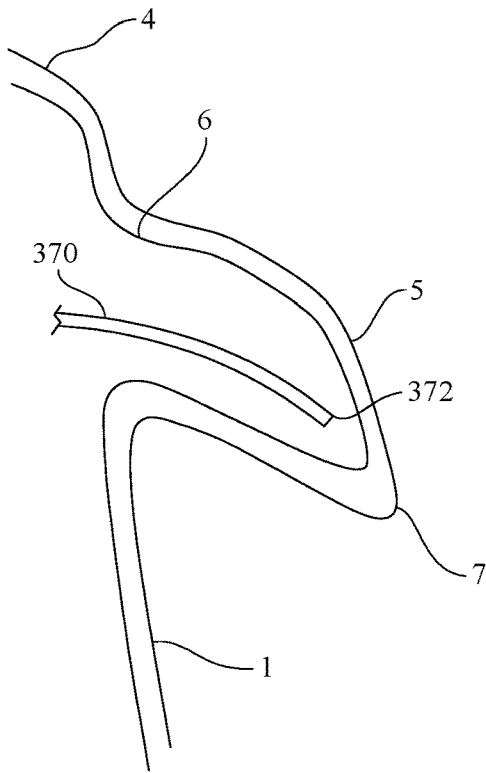
Figure 13C:
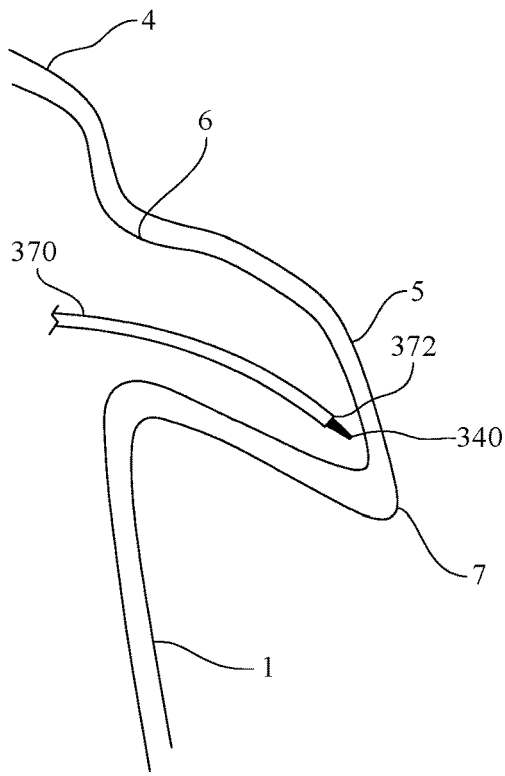
Figure 13D:
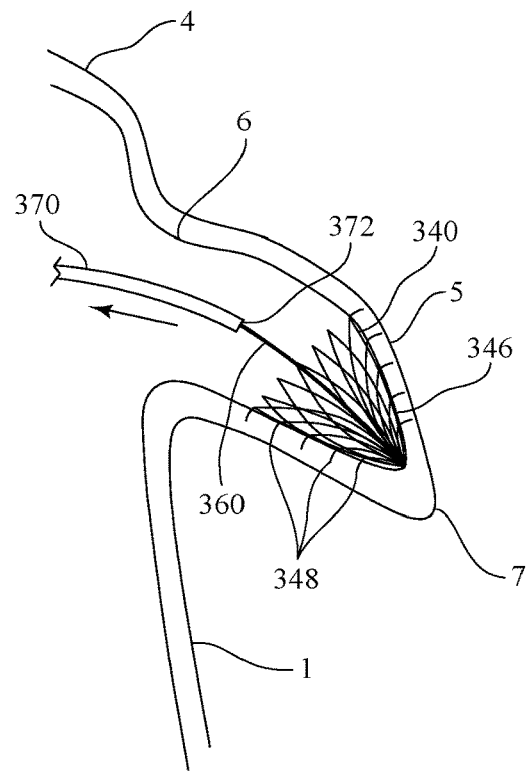
Figure 13E:
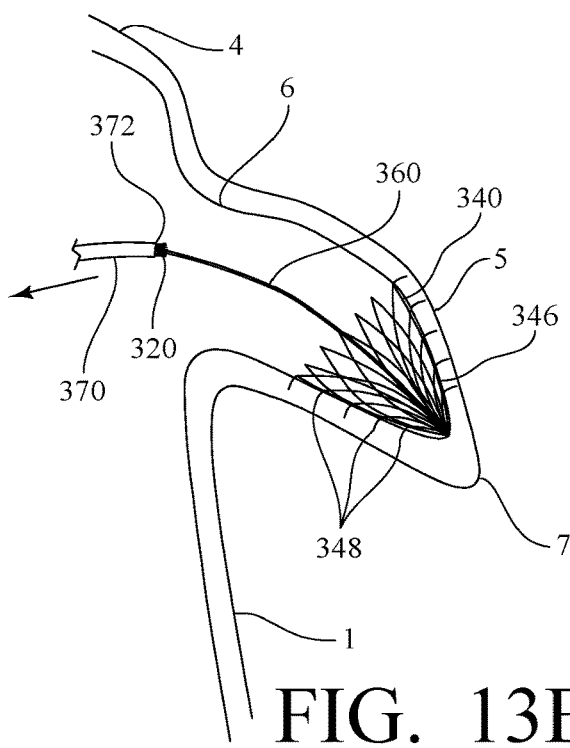
Figure 13F:
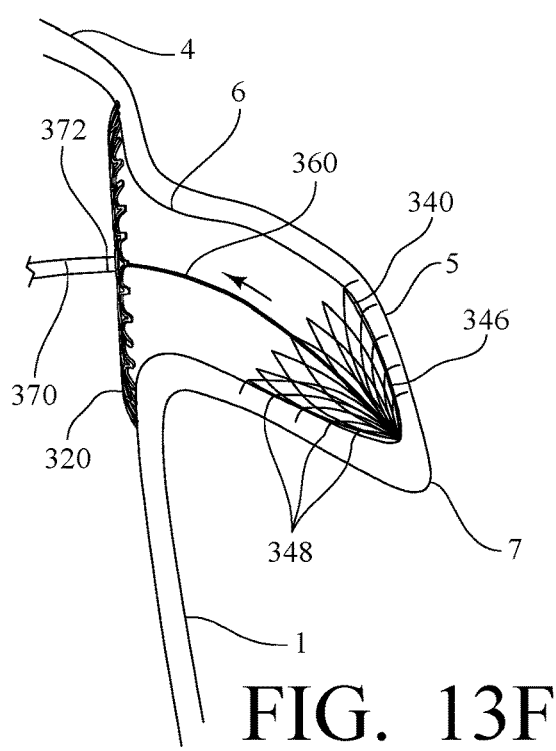
Figure 13G:
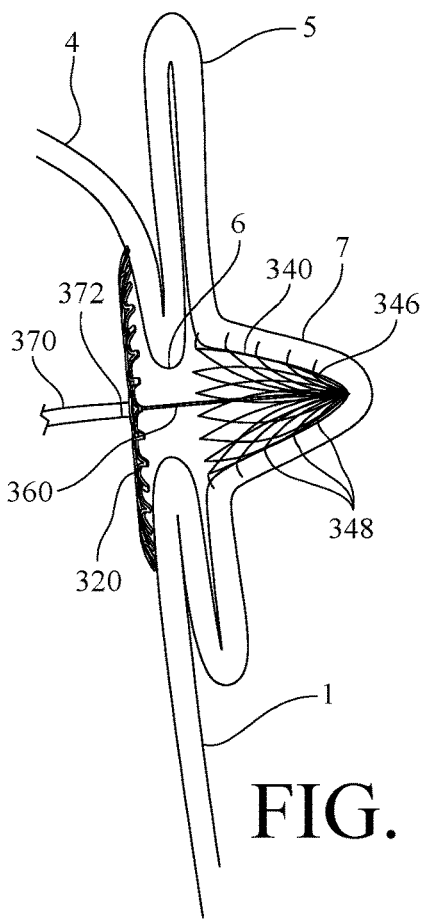
Figure 13H:
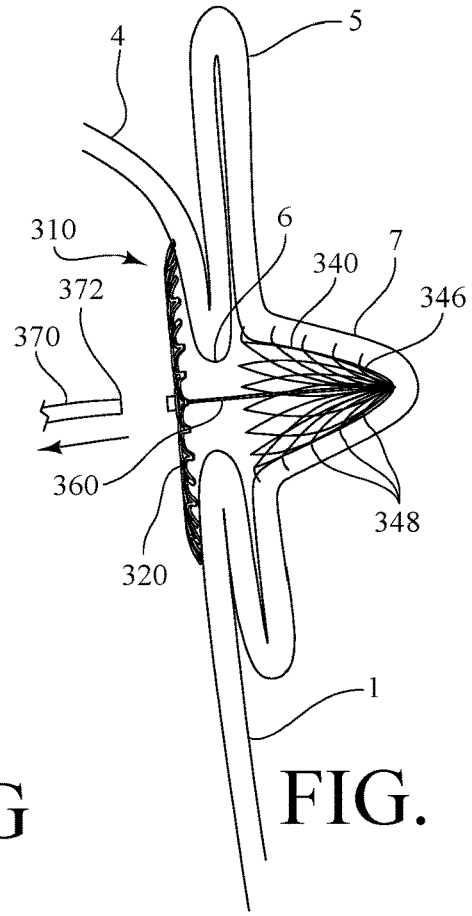

FIGS. 13A-13H depict another exemplary implementation of the method of occluding a left atrial appendage of a heart of the present invention substantially the same as the method shown in FIGS. 12A-12H except that in the method shown in FIGS. 13A-13H, the anchoring portion 340 of the exemplary atrial appendage closure device 310 does not continue to open until it is a substantially flat disc when pulled toward the occluding portion 320. Instead, the anchoring portion 340 maintains substantially the same conical shape, as shown in FIGS. 13G and 13H. All other features of the method depicted in FIGS. 13A-13H are the same as the method shown in FIGS. 12A-12H.

Figure 14A:
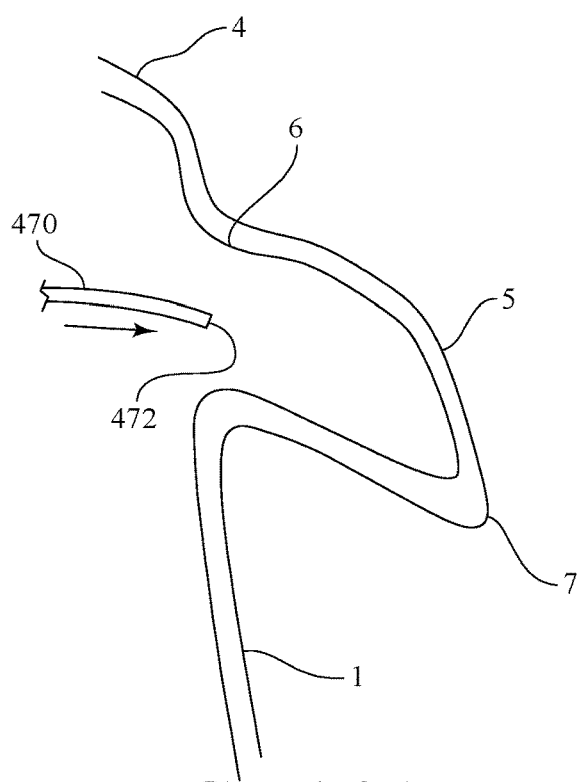
FIGS. 14A-14H are a series of schematic representations of another exemplary method of occluding a left atrial appendage in accordance with the presently-disclosed subject matter, in which another atrial appendage closure device similar to the atrial appendage closure device of FIG. 11 is deployed to provide a seal between the left atrial appendage and the left atrium of a heart.
Figure 14B:
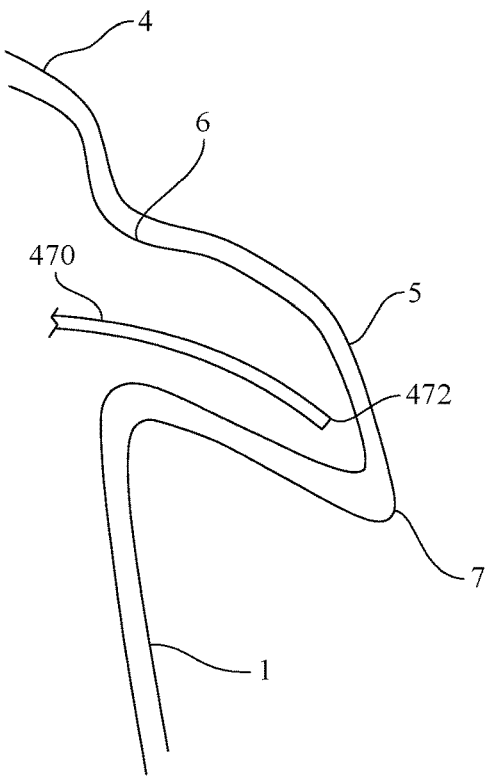
Figure 14C:
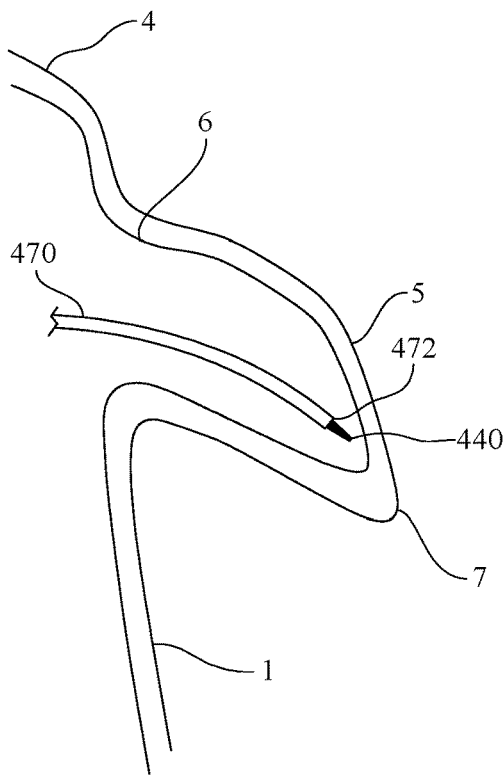
Figure 14D:
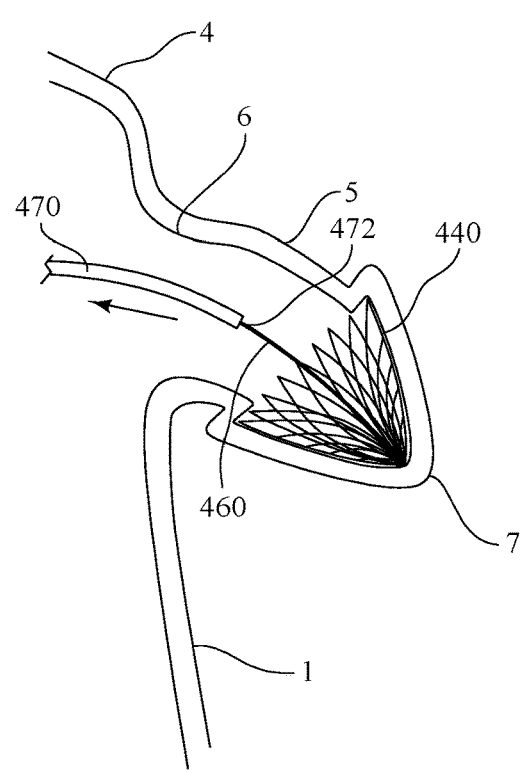
Figure 14E:
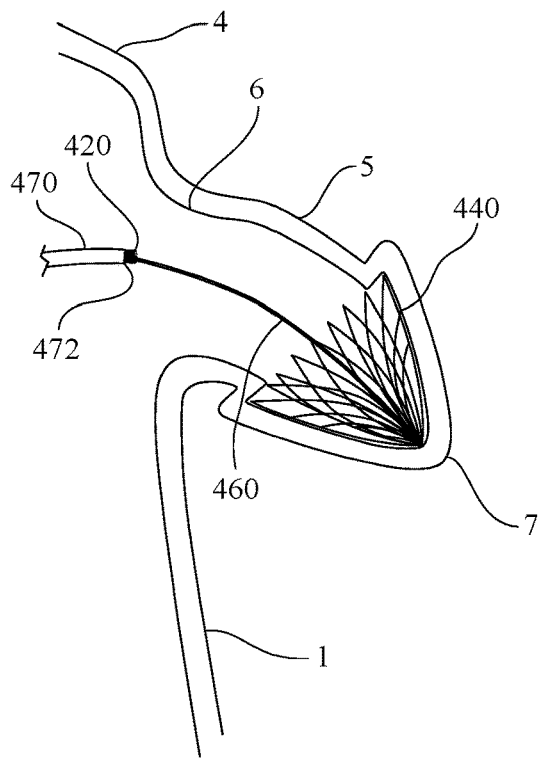
Figure 14F:
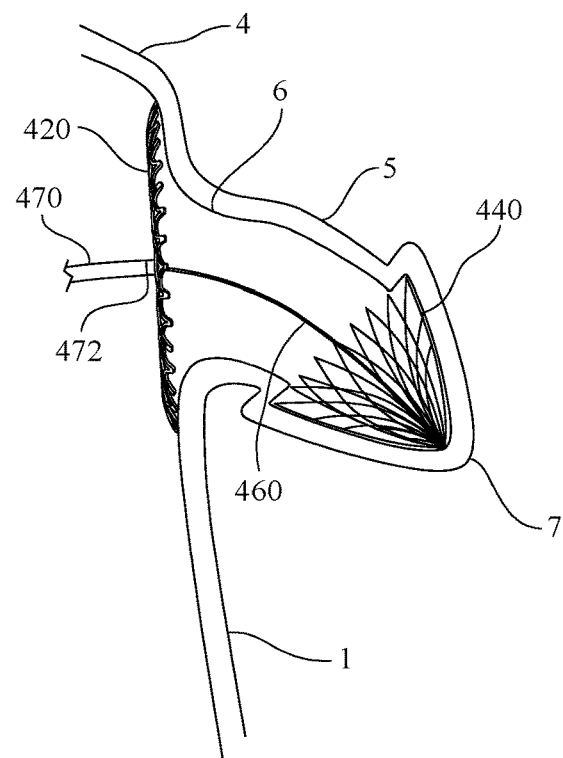
Figure 14G:
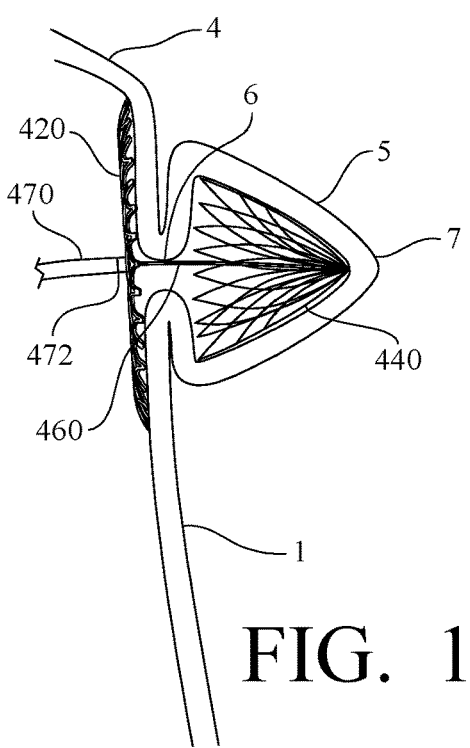
Figure 14H:
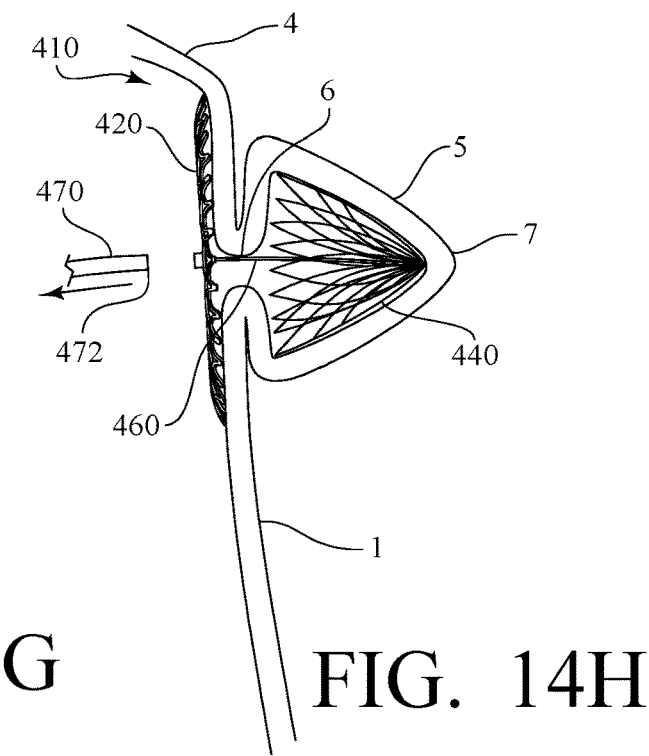

FIGS. 14A-14H depict yet another exemplary implementation of the method of occluding a left atrial appendage of a heart of the present invention substantially the same as the method shown in FIGS. 12A-12H except that, in the method shown in FIGS. 14A-14H, the anchoring portion 440 of the exemplary atrial appendage closure device 410 does not have any barbs extending away from the distal surface 446 of the anchoring portion 440. Instead, as shown in FIGS. 14D-14F, the anchoring portion 440 has sufficient stored energy to cause the left atrial appendage to bulge outward when the anchoring portion 440 is positioned within the left atrial appendage 5 and to thus secure the anchoring portion 440 within the left atrial appendage 5. Furthermore, and similar to the method shown in FIGS. 13A-13H, in the method shown in FIGS. 14A-14H, the anchoring portion 440 does not continue to open until it is a substantially flat disc when the anchoring portion 440 is pulled toward the occluding portion 420. Instead, the anchoring portion 440 maintains substantially the same umbrella-like shape, as shown in FIGS. 14G and 14H. All other features of the method depicted in FIGS. 14A-14H are the same as the method shown in FIGS. 12A-12H.

Figure 15:
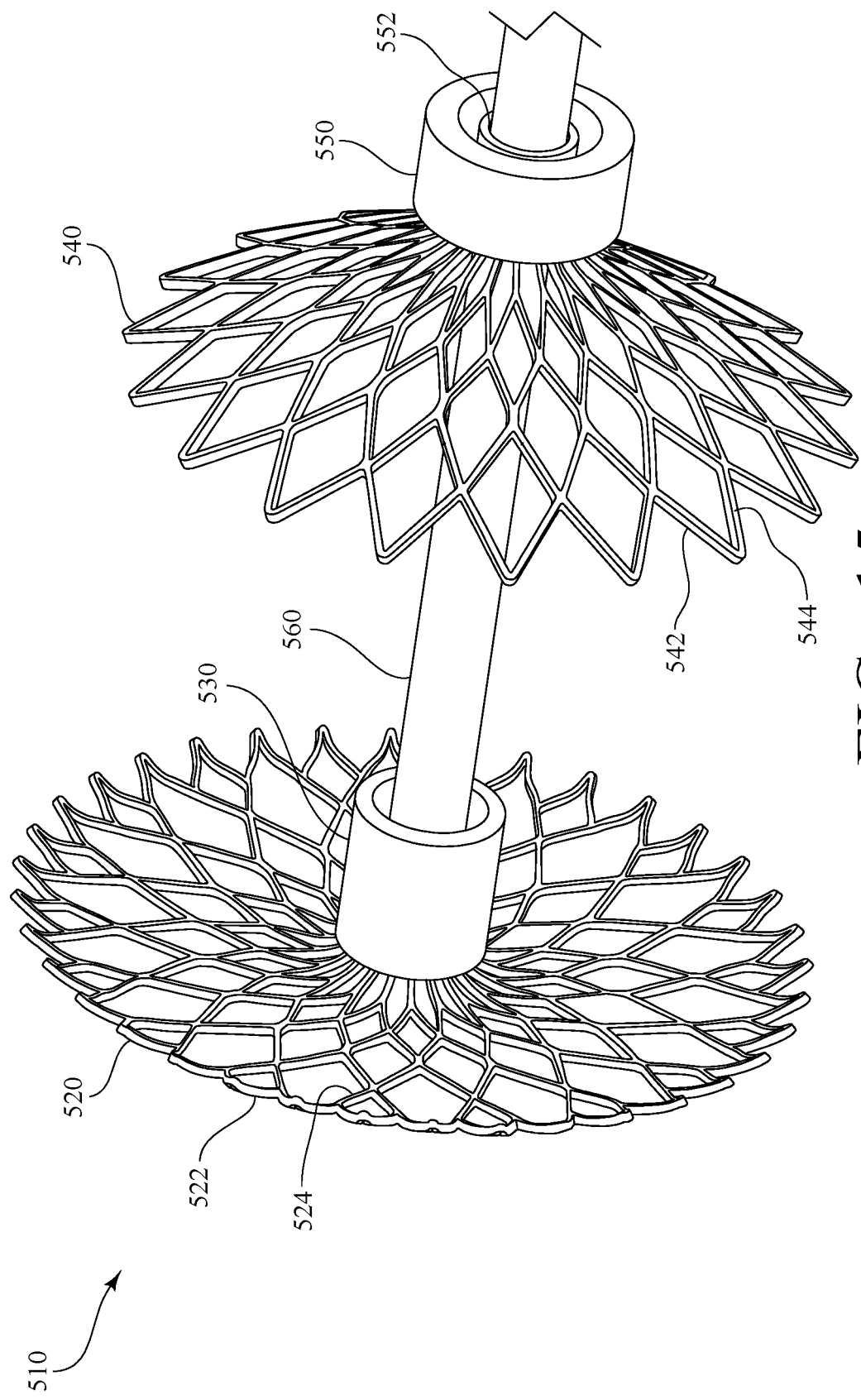
FIG. 15 is a perspective view of another exemplary atrial appendage closure device made in accordance with the present invention and including an occluding portion in a deployed position and an anchoring portion in a deployed position.
Figure 16:
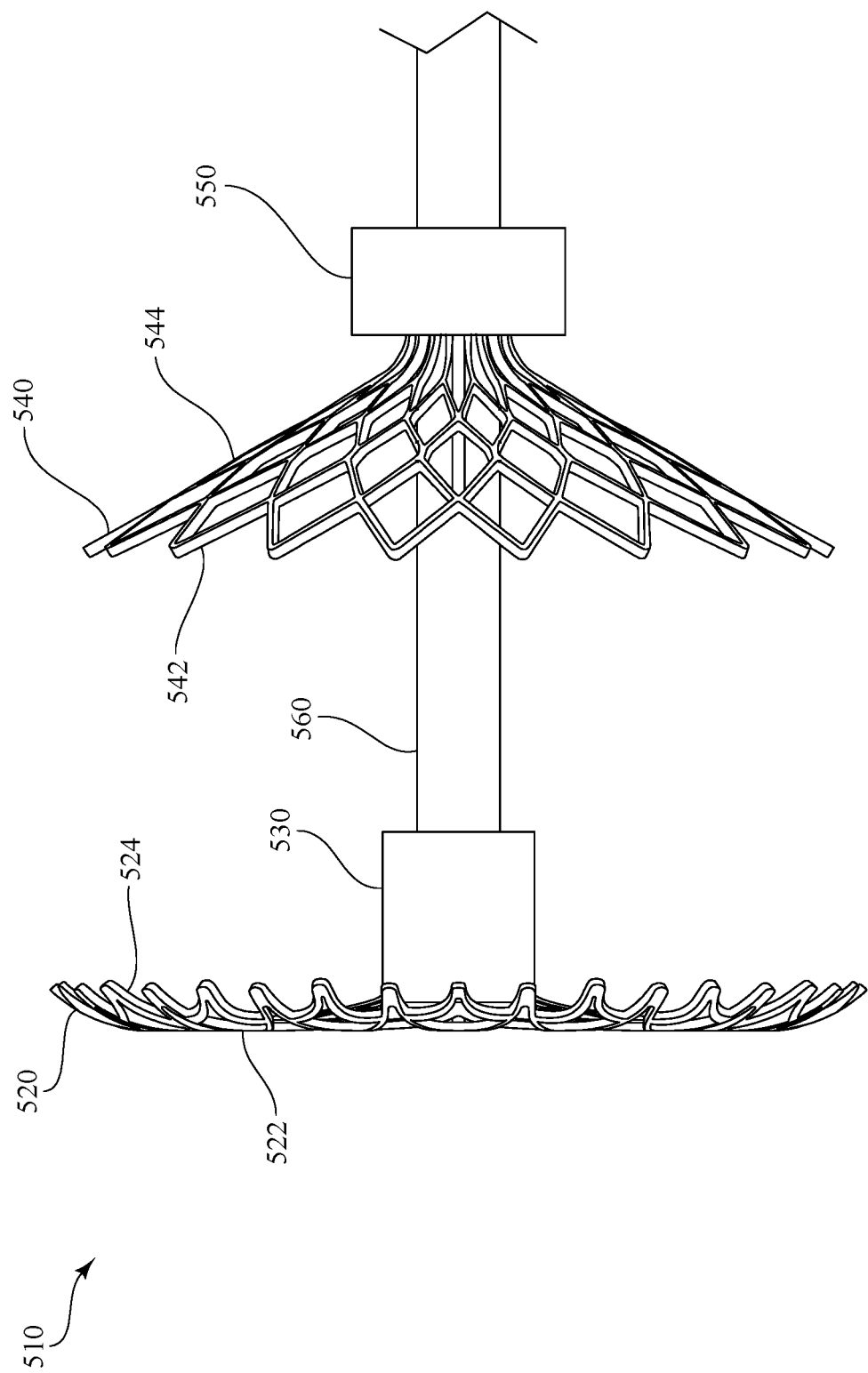
FIG. 16 is a side view of the atrial appendage closure device of FIG. 15.
Figure 17:
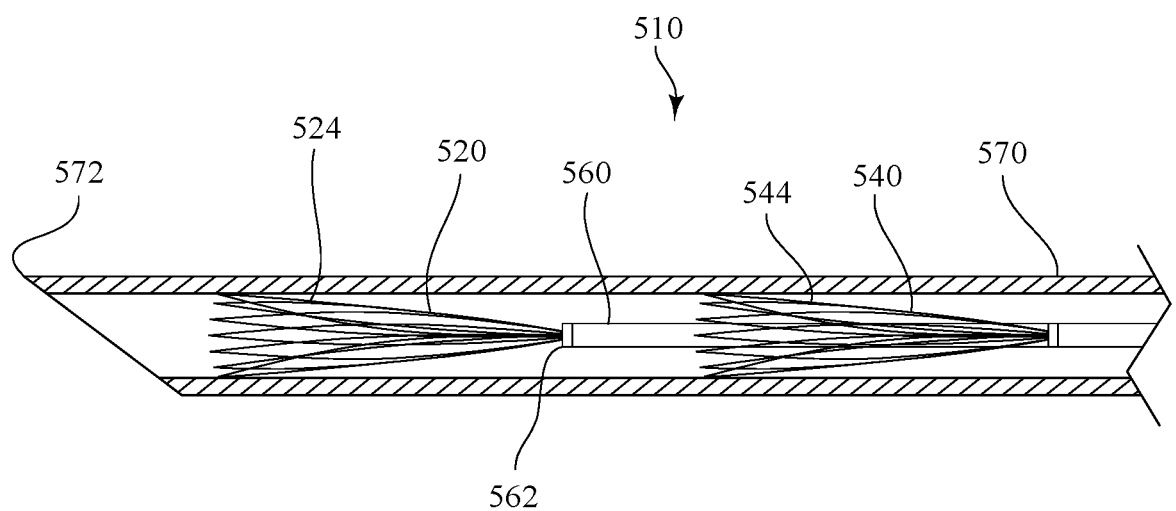
FIG. 17 is a side view of the atrial appendage closure device of FIG. 15 positioned within a large bore needle and with the occluding member schematically represented in a forward facing retracted position and the anchoring portion schematically represented in a forward facing retracted position.

Referring now to FIGS. 15-17, another exemplary atrial appendage closure device 510 made in accordance with the presently-disclosed subject matter includes an occluding portion 520 and an anchoring portion 540 that are both comprised of a collapsible frame in a starburst pattern. More specifically, in the embodiment shown in FIGS. 15-17, the occluding portion 520 has a distal surface 522 and a proximal surface 524 opposite the distal surface 522 and the anchoring portion 540 has a distal surface 544 and a proximal surface 542 opposite the distal surface 544 with the proximal surface 542 of the anchoring portion 540 facing the proximal surface 524 of the occluding portion 520. As also shown in FIGS. 15-17, the occluding portion 520 has a hub 530 with an insertion rod 560 that is connected to the hub 530 of occluding portion 520 on the proximal surface side of the occluding portion 520. Furthermore, the anchoring portion 540 has a hub 550 defining a hole 552 and the insertion rod 560 extends away from the occluding portion 520 with the hole 552 defined through the hub 550 of the anchoring portion 540 configured to accept the insertion rod 560, allowing the anchoring portion 540 to slide along the length of the insertion rod 560, as further discussed below.

In this embodiment, both the occluding portion 520 and an anchoring portion 540 are movable between a retracted position and a deployed position. Unlike previous embodiments, and as shown in FIG. 17, this exemplary atrial appendage closure device 510 is implanted into a subject with a large bore needle 570. By making use of an occluding portion 520 and anchoring portion 540 that are moveable between a retracted position and a deployed position, the occluding portion 520 of the device 510 can advantageously be placed into its retracted position and subsequently inserted into the left atrial appendage 5 of a heart 1 with only a minimally invasive thoracotomy with a small (e.g., approximately 1 inch) incision, similar to those used in laparoscopic procedures.

As shown in FIG. 17, in which the device 510 is provided within a large bore needle 570, when the occluding portion 520 is in the retracted position, the occluding portion 520 is collapsed away from the anchoring portion 540, and when the anchoring portion 540 is in the retracted position, the anchoring portion 520 is collapsed toward the occluding portion 520. In other words both the occluding portion 520 and the anchoring portion 540 face towards the open end 572 of the needle 570. Although the anchoring portion 540 is shown positioned within the needle 570 simultaneously with the occluding portion 520, as discussed below, in some embodiments the occluding portion 520 can be implanted before the anchoring portion 540 is positioned within the needle 570.

With regard to the insertion rod 560 of the exemplary atrial appendage closure device 510, the insertion rod 560 is in the form of a solid rod and is generally constructed from a metal or plastic material to provide an insertion rod having a sufficient strength to allow it to be inserted through the wall of a left atrial appendage of a heart and retain its shape. However, as a refinement to the atrial appendage closure devices of the presently-disclosed subject matter and, in particular, to the insertion rods of the devices, in a further embodiment, the insertion rod can define a hollow interior cavity and with a plurality of fenestrations that are in fluid communication with the hollow interior cavity of the insertion rod. Further details regarding insertion rods, such as the insertion rod 560 of the exemplary atrial appendage closure device 510, can be found in International Patent Application No. PCT/US2013/052362, filed on Jul. 26, 2013, which is herein incorporated by reference.

Referring now to FIGS. 18A-18J, in another exemplary implementation of the method of occluding a left atrial appendage of a heart of the present invention, a needle 570 is first provided which can accept an atrial appendage closure device 510 with the occluding portion 520 and the anchoring portion 540 both in a retracted position, as shown in FIG. 17.

Figure 18A:
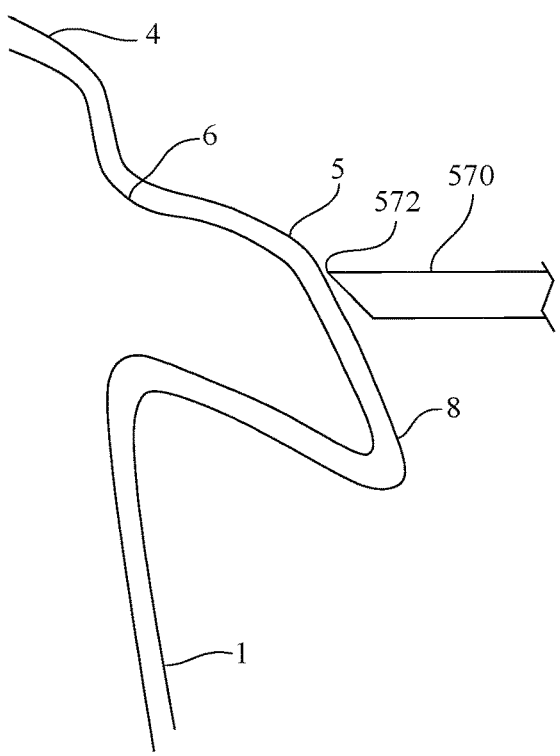
FIGS. 18A-18J are a series of schematic representations of another exemplary method of occluding a left atrial appendage in accordance with the presently-disclosed subject matter, in which the atrial appendage closure device of FIG. 15 is deployed to provide a seal between the left atrial appendage and the left atrium of a heart.
Figure 18B:
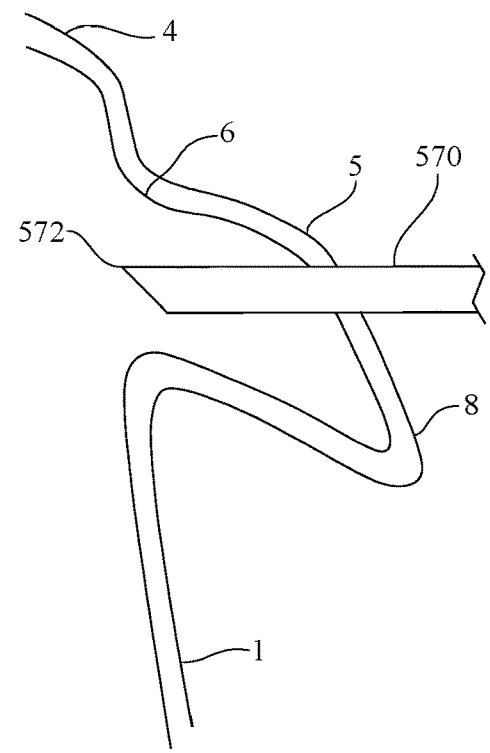

As shown in FIGS. 18A and 18B, unlike the previous methods described above, according to this method of occluding a left atrial appendage, the large bore needle 570 is first used to pierce through the wall 8 of a left atrial appendage 5 from the exterior of the heart 1 until the open end 572 of the needle 570 is positioned within the left atrium 4.

Figure 18C:
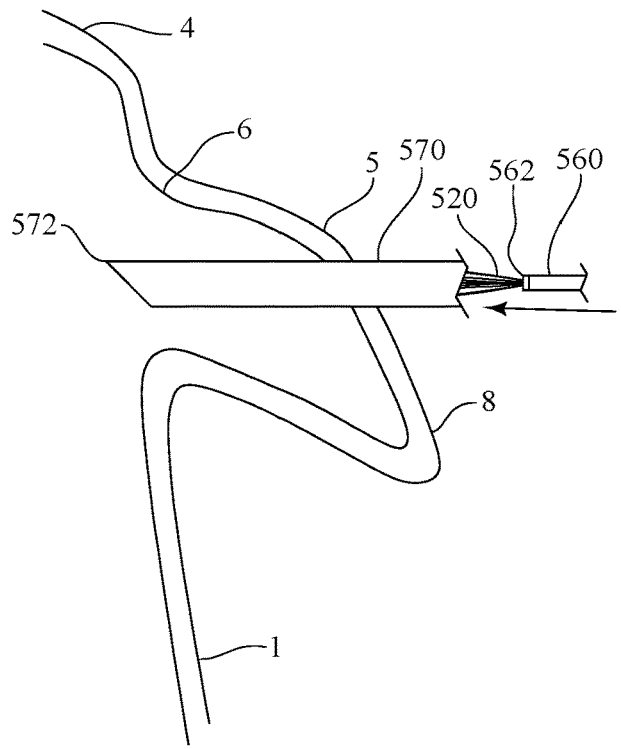
Figure 18D:
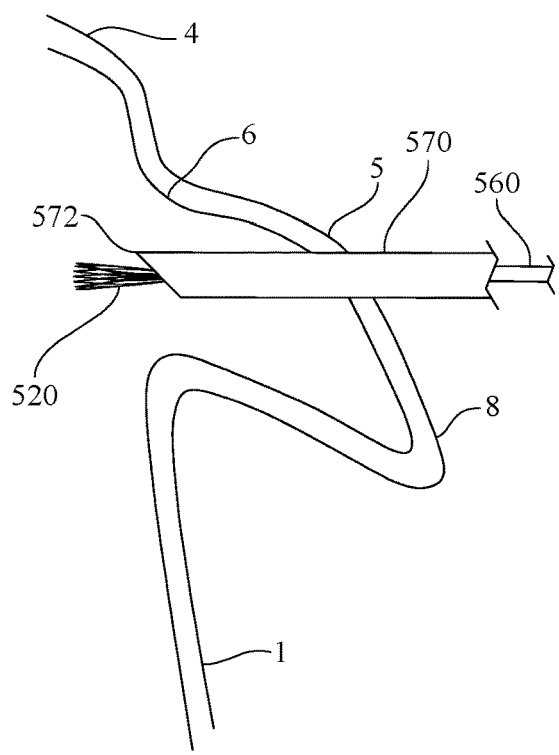

Referring now to FIGS. 18C-18D, the portion of the atrial appendage closure device 510 that includes the occluding portion 520 and attached insertion rod 560 is then provided. The occluding portion 520 is placed in a retracted position and the retracted occluding portion 520 is then inserted through the large bore needle 570 along with the first end 562 of the insertion rod 560 until the occluding portion 520 is sufficiently placed in the left atrium 4.

Figure 18E:
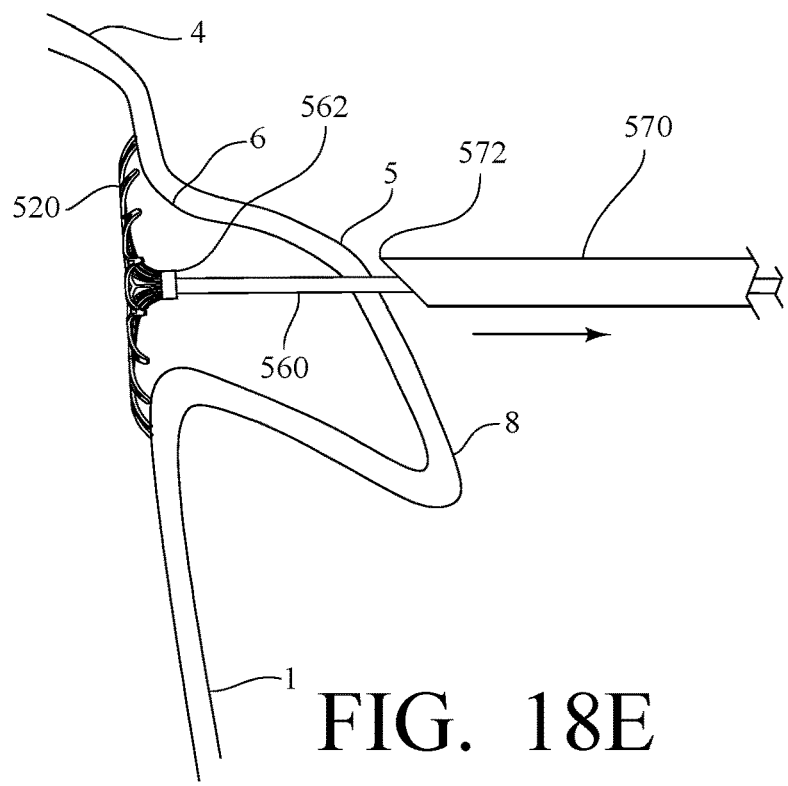

Referring now to FIG. 18E, the occluding portion 520 is deployed inside the left atrium 4 forming a seal across the orifice 6 of the left atrial appendage 5, and the large bore needle 570 is then retracted from the wall 8 of the left atrial appendage 5.

Figure 18F:
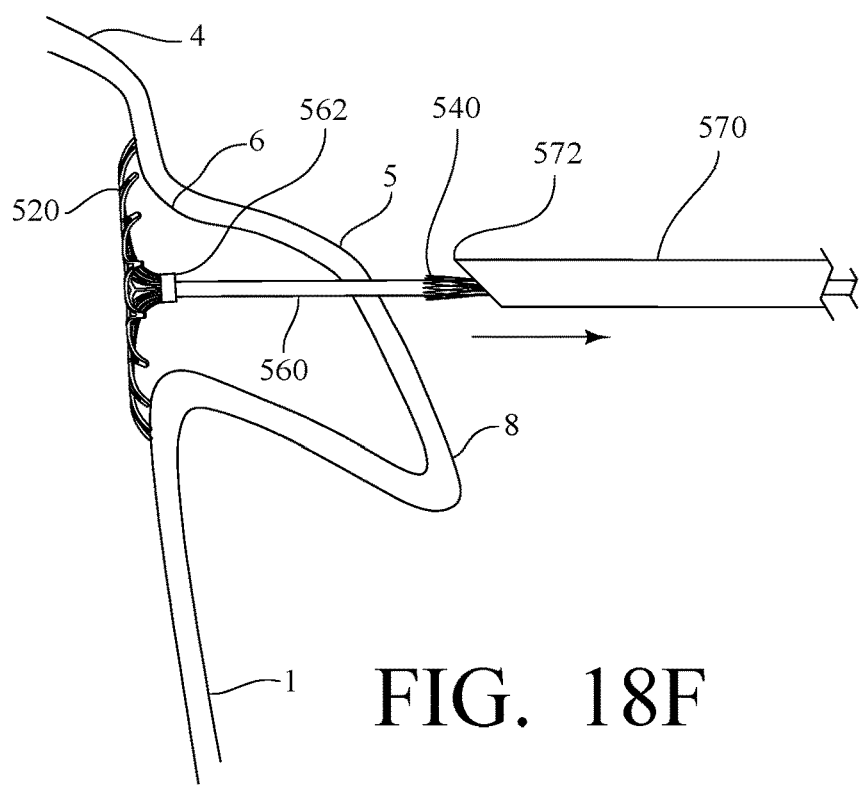
Figure 18G:
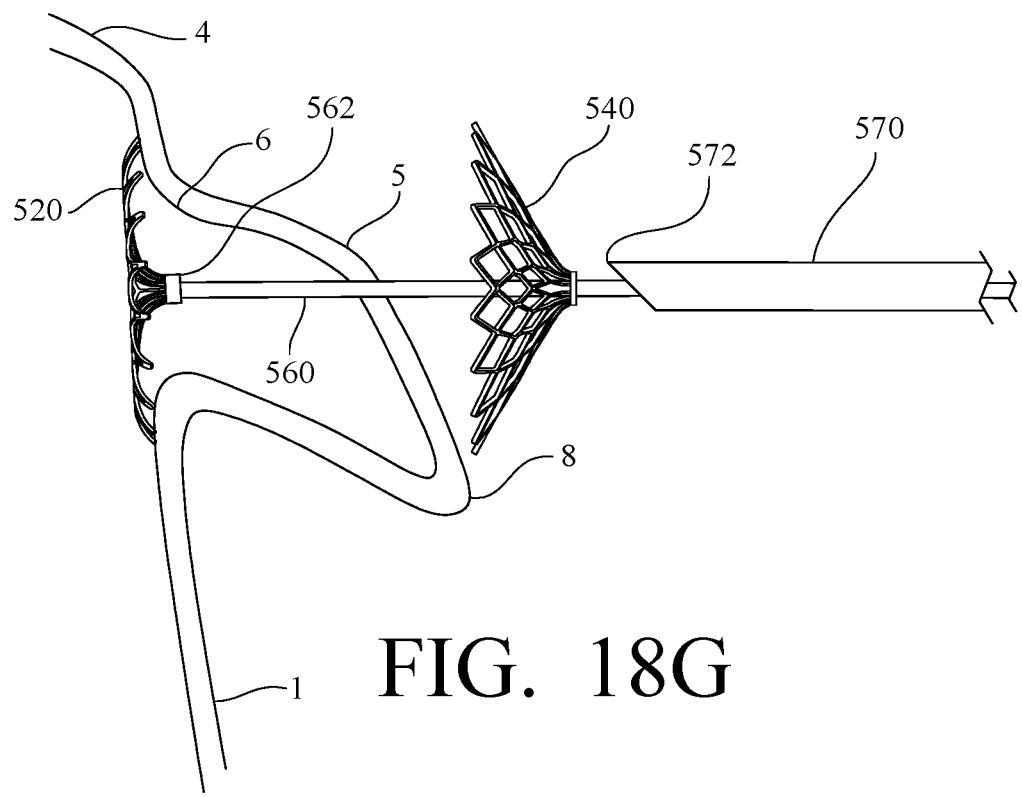
Figure 18H:
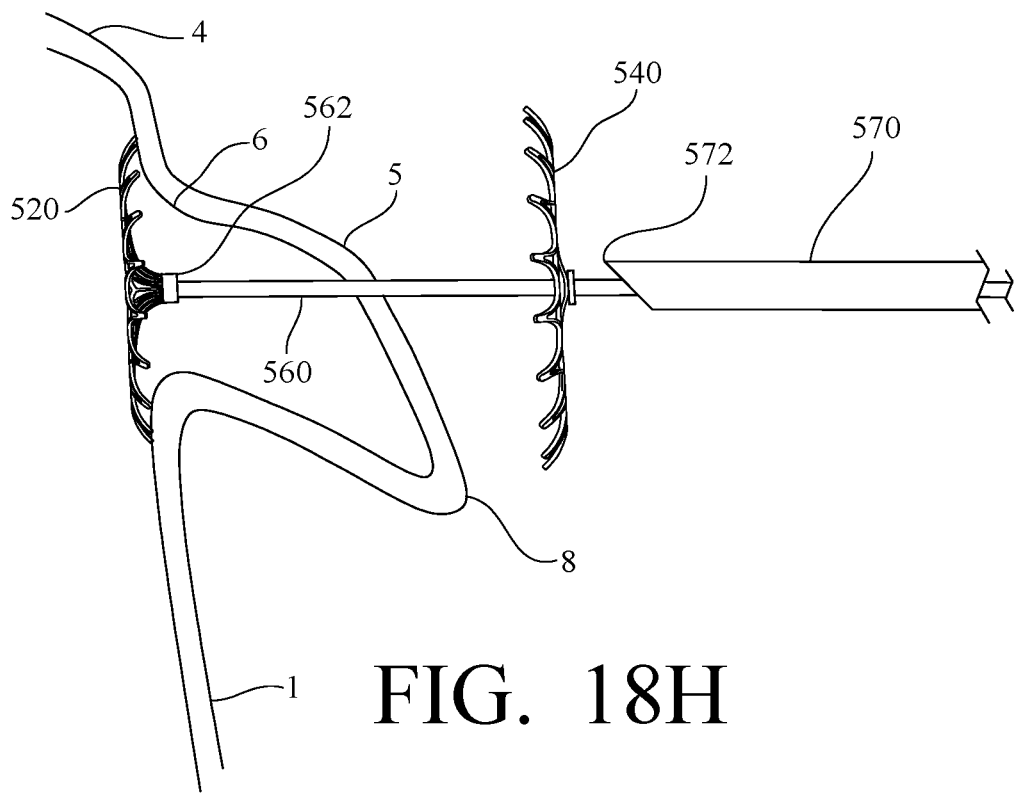

Referring now to FIGS. 18F-18H, subsequent to retracting the needle 570 from the wall 8 of the left atrial appendage 5, the anchoring portion 540 is then provided and placed in a retracted position onto the second end (not shown) of the insertion rod 560 opposite the first end 562 of the insertion rod 560 and the anchoring portion 540 is slid along the length of the insertion rod 560 within the needle 570. The anchoring portion 540 is then advanced out of the needle 570 and deployed outside of the heart 1.

Figure 18I:
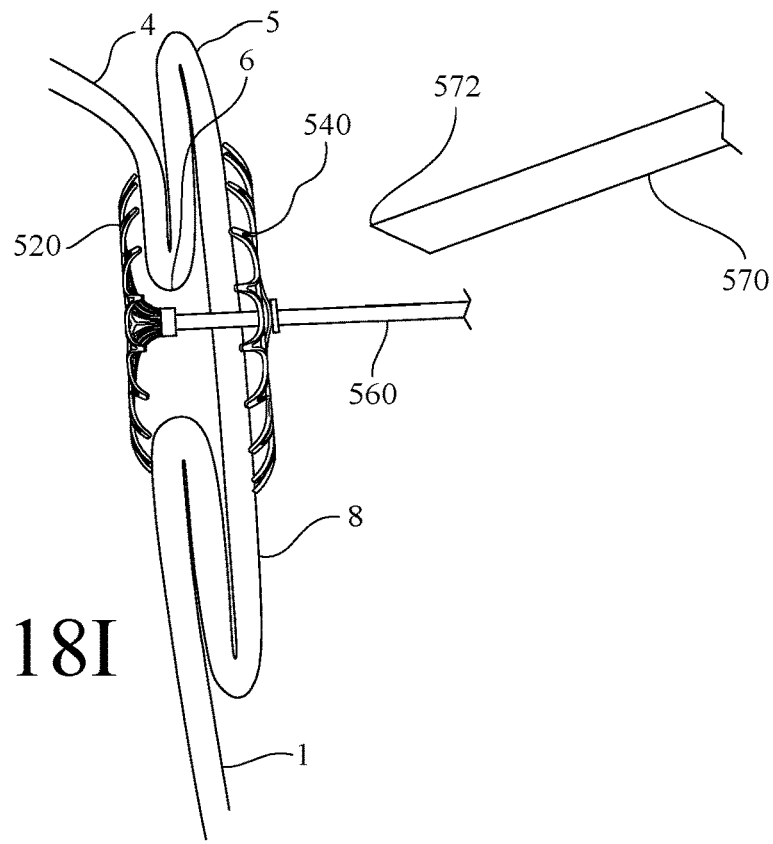
Figure 18J:
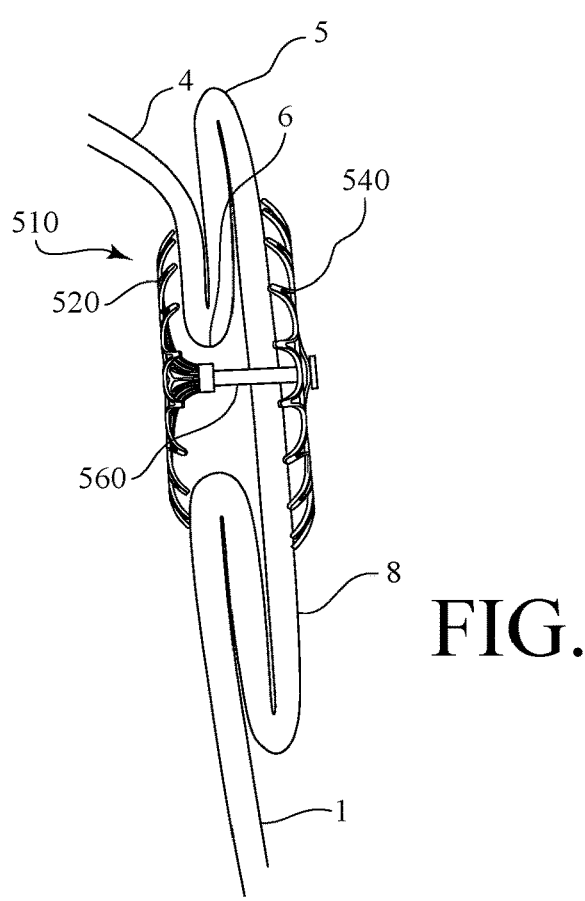

Referring now to FIGS. 18I-18J, by pushing the anchoring portion 540 along the insertion rod 560 and against the wall 8 of the left atrial appendage 5 opposite the occluding portion 520, the left atrial appendage 5 is then collapsed and the large bore needle 570 is removed from the insertion rod 560. Once again, it should be understood that the distance between the anchoring portion 540 and the occluding portion 520 is fully adjustable such that any degree of compression of the left atrial appendage 5 is possible. After securing the anchoring portion 540 to the insertion rod 560, the insertion rod 560 is cut away or otherwise broken adjacent to the anchoring portion 540 to finish the occlusion of the left atrial appendage 5.

Figure 19:
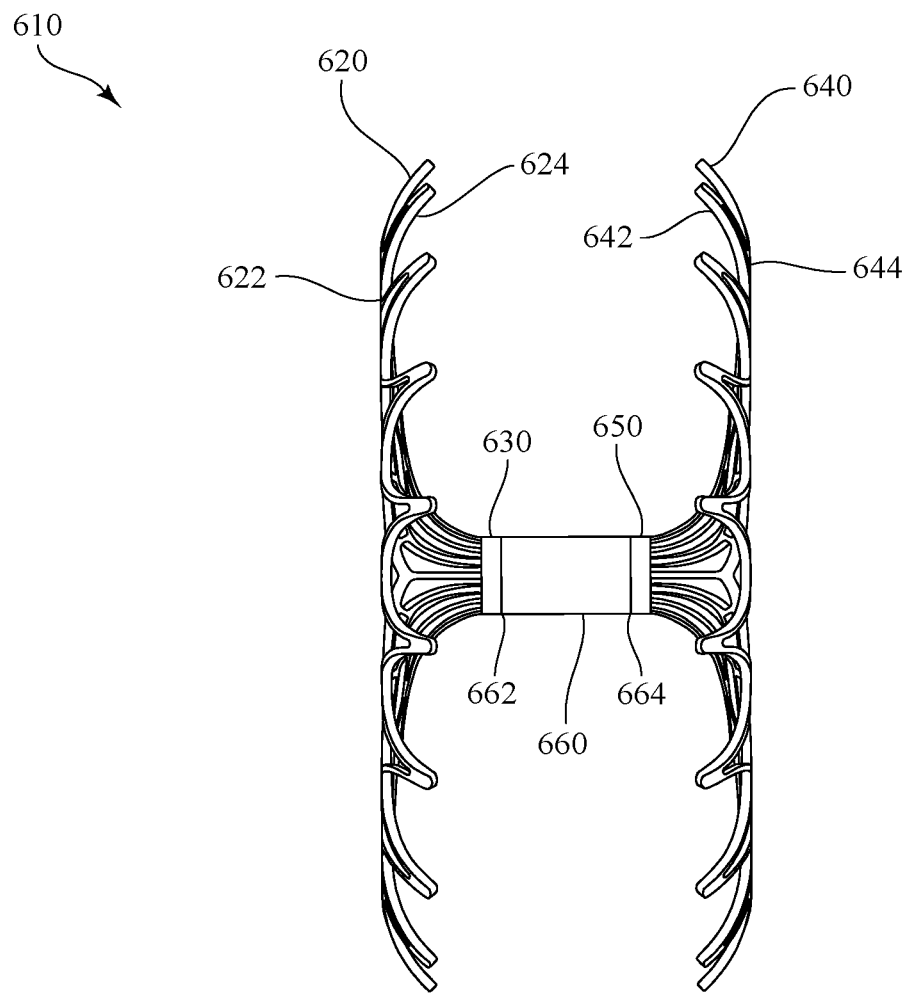
FIG. 19 is a perspective view of another exemplary atrial appendage closure device made in accordance with the present invention and including an occluding portion in a deployed position and an anchoring portion in a deployed position.
Figure 20:
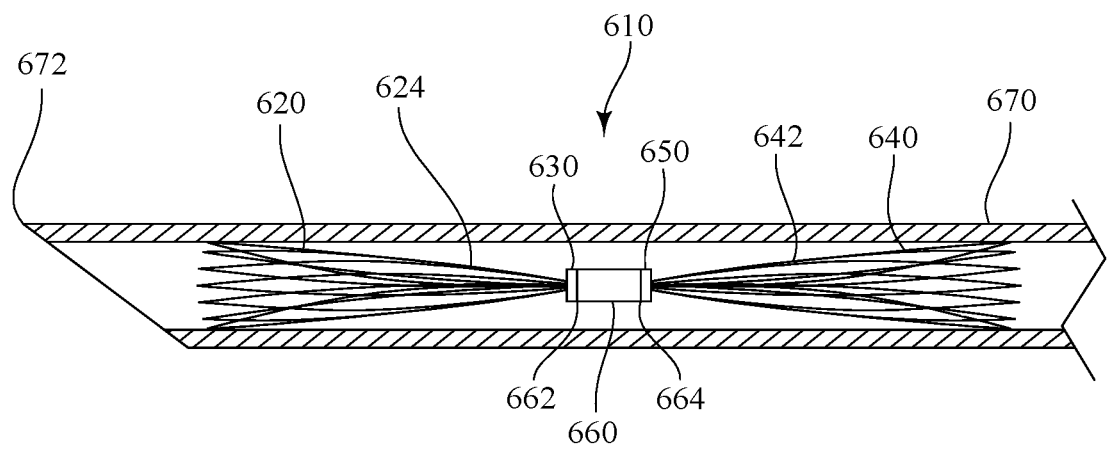
FIG. 20 is a side view of the atrial appendage closure device of FIG. 19 positioned within a delivery catheter and with the occluding portion schematically represented in a forward facing retracted position and the anchoring portion schematically represented in a rearward facing retracted position.

Referring now to FIGS. 19-20, in another exemplary embodiment of the present invention, an atrial appendage closure device 610 includes an occluding portion 620 and an anchoring portion 640 with a central post 660 positioned between connecting the occluding portion 620 and the anchoring portion 640. Both the occluding portion 620 and the anchoring portion 640 are comprised of a collapsible frame in a starburst pattern, similar to embodiments described above. More specifically, in the embodiment shown in FIGS. 19-20, the occluding portion 620 has a distal surface 622 and a proximal surface 624 opposite the distal surface 622 and the anchoring portion 640 has a distal surface 644 and a proximal surface 642 opposite the distal surface 644 with the proximal surface 642 of the anchoring portion 640 facing the proximal surface 624 of the occluding portion 620. The central post 660 has a first end 662 connected to a hub 630 of the occluding portion 620 on the proximal surface side of the occluding portion 620, and a second end 664 connected to a hub 650 of the anchoring portion 640 on the proximal surface side of the anchoring portion 640.

In this embodiment, both the occluding portion 620 and the anchoring portion 640 are also movable between a retracted position and a deployed position. As shown in FIG. 19, when in the deployed position, both the occluding portion 620 and the anchoring portion 640 extend outward to form a substantially flat disc. As shown in FIG. 20, when the occluding portion 620 is in the retracted position, the occluding portion 620 is collapsed away from the anchoring portion 640, and similarly when the anchoring portion 640 is in the retracted position, the anchoring portion 620 is collapsed away from the occluding portion 620. In other words both the occluding portion 620 and the anchoring portion 640 face away from each other.

With regard to the central post 660, the length of the central post 660, and thus the spacing between the occluding portion 620 and the anchoring portion 640, is not limited and can be selected based, at least in part, on the thickness of the walls of the left atrium 4 and/or the left atrial appendage 5 of a patient.

Figure 21A:
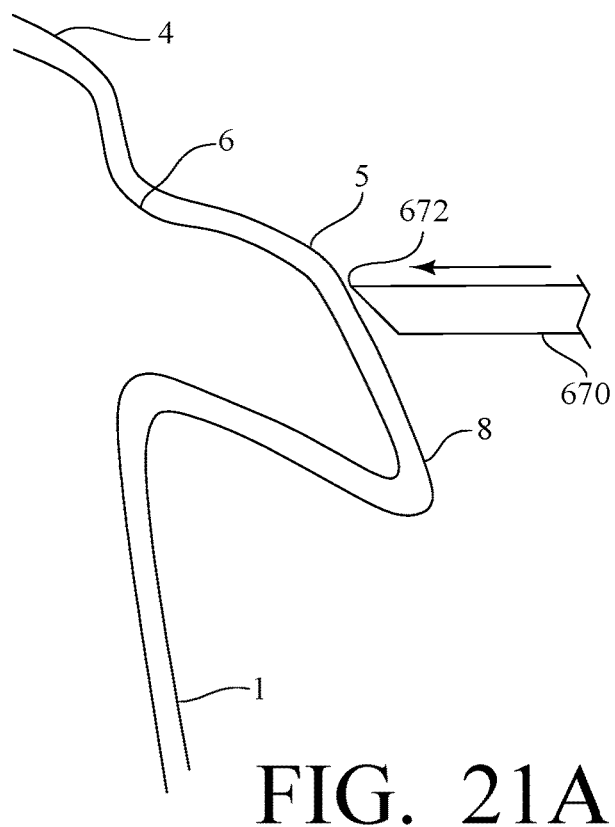
FIGS. 21A-21G are a series of schematic representations of another exemplary method of occluding a left atrial appendage in accordance with the presently-disclosed subject matter, in which the atrial appendage closure device of FIG. 19 is deployed to provide a seal between the left atrial appendage and the left atrium of a heart.
Figure 21B:
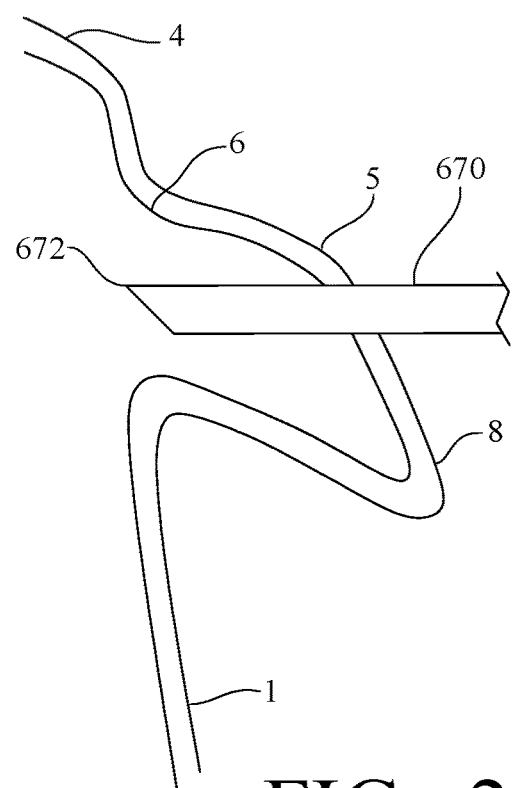

Referring now to FIGS. 21A-21G, in another exemplary implementation of the method of occluding a left atrial appendage of a heart of the present invention, the method is substantially the same as the method shown in FIGS. 18A-18J except that the occluding portion 620 and the anchoring portion 640 are connected as shown in FIGS. 19-20 and therefore are inserted through the large bore needle 670 simultaneously. Specifically, as shown in FIGS. 21A and 21B, like the previous methods described above, according to this method of occluding a left atrial appendage, the large bore needle 670 is first pierced through the wall 8 of a left atrial appendage 5 from the exterior of the heart 1 until the open end 672 of the needle 670 is positioned within the left atrium 4.

Figure 21C:
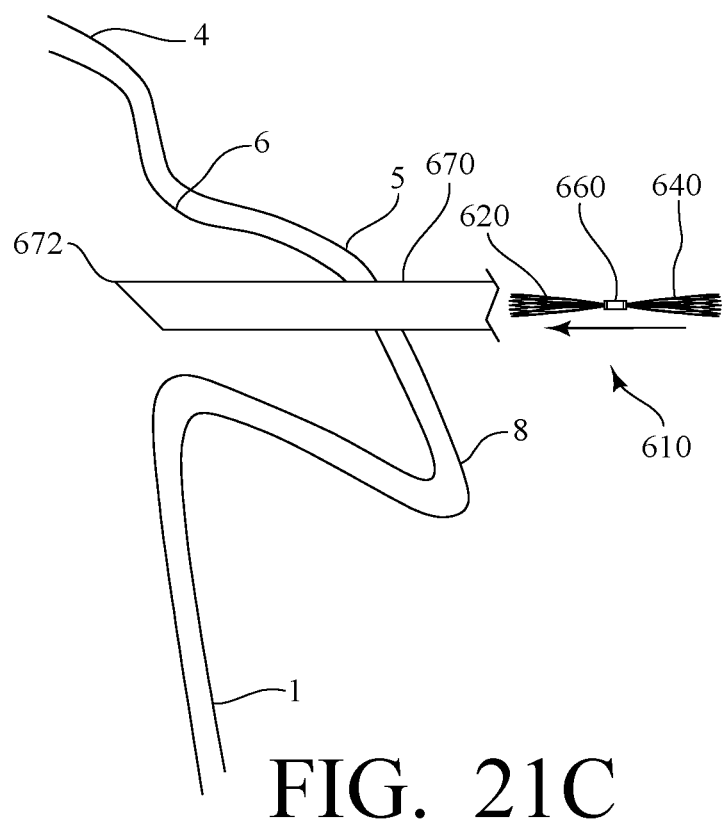
Figure 21D:
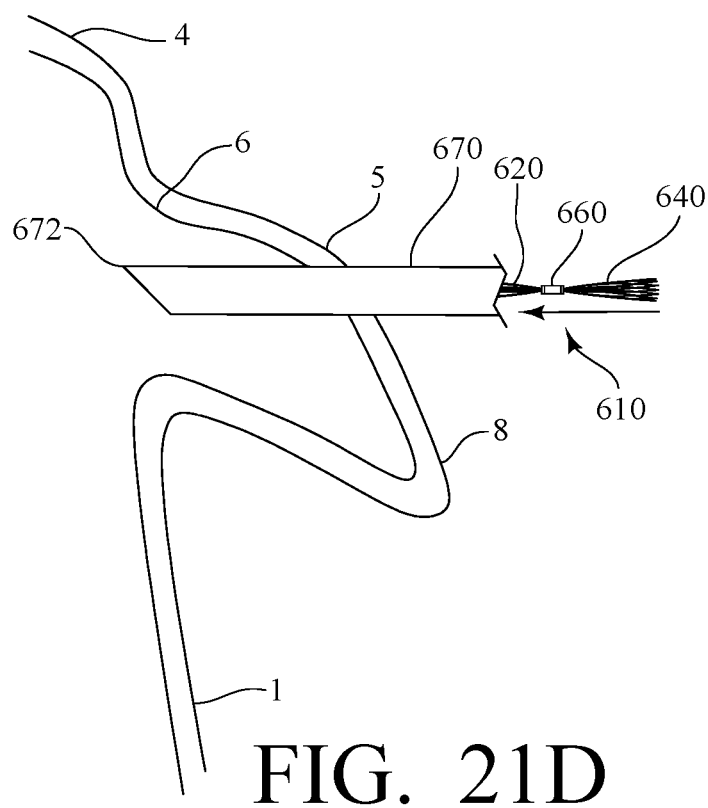

Referring now to FIGS. 21C-21D, the atrial appendage closure device 610 comprising the occluding portion 620, the anchoring portion 640, and the central post 660 is then provided with the occluding portion 620 and the anchoring portion 640 placed in a retracted position.

Figure 21E:
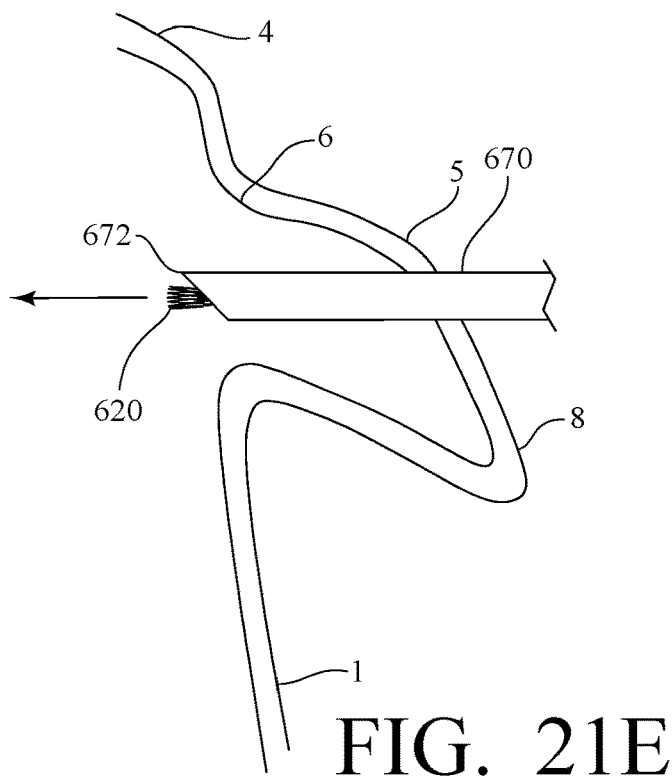
Figure 21F:
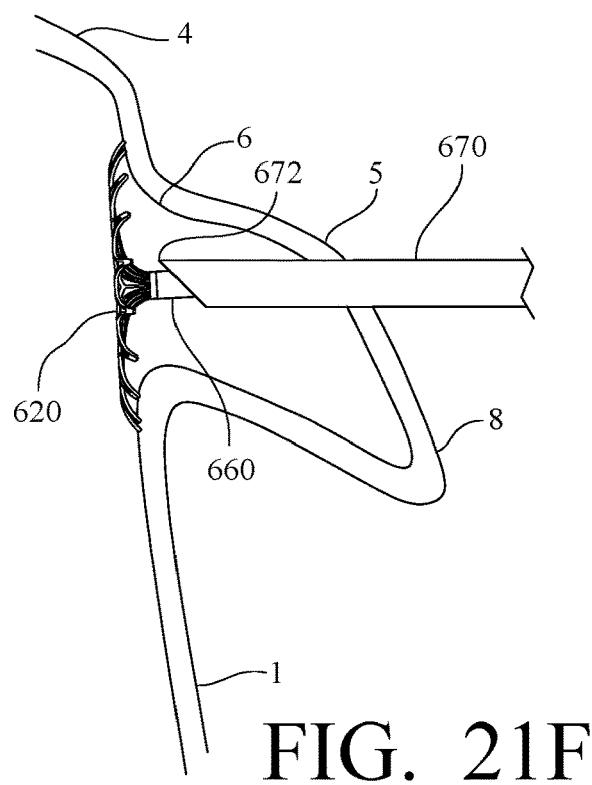

Referring now to FIGS. 21E-21F, the device 610 is then inserted through the large bore needle 670 until the occluding portion 620 is sufficiently placed in the left atrium 4 and the occluding portion 620 is deployed inside the left atrium 4 forming a seal across the orifice 6 of the left atrial appendage 5. The large bore needle 670 is then retracted from the wall 8 of the left atrial appendage 5 exposing the central post 660 of the atrial appendage closure device 610.

Figure 21G:
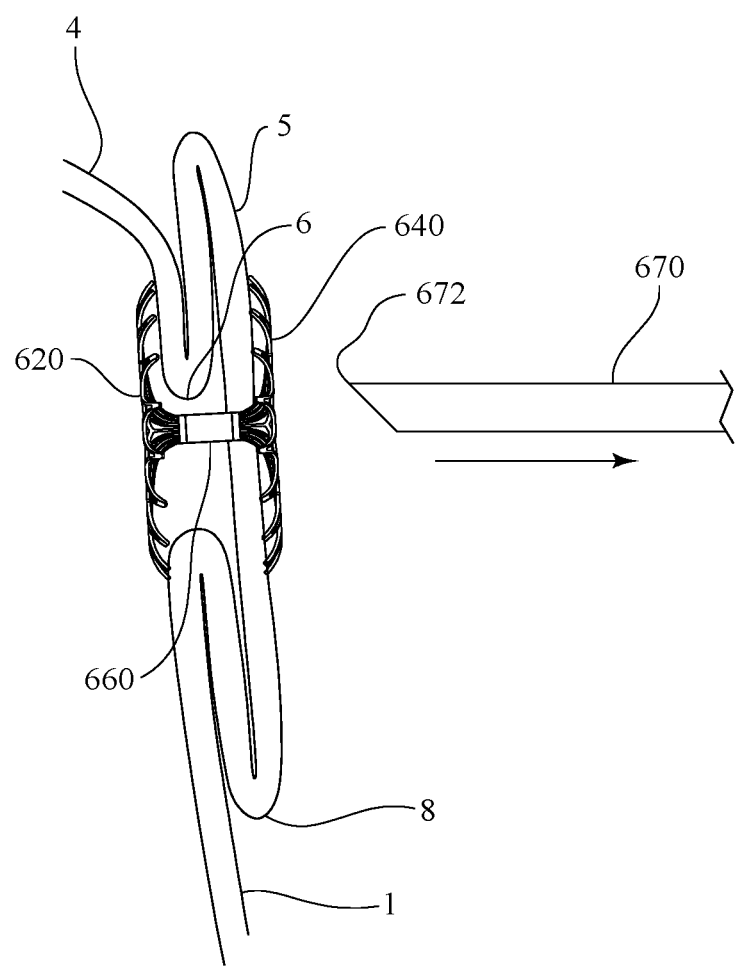

Referring now to FIG. 21G, simultaneously with the retraction of the needle 670 from the wall 8 of the left atrial appendage 5, the anchoring portion 640 is advanced out of the needle 670 and deployed outside of the heart.

With further respect to the devices and methods described herein, it should be understood that although the exemplary implementations of the methods of the present invention only depict the insertion and implantation of an exemplary atrial appendage closure device, it is contemplated that, in some embodiments, after each of the above the devices is implanted, the device can be repositioned and/or withdrawn if necessary. Specifically, each of the above occluding portions and anchoring portions can be returned, fully or partially, to the retracted position from the deployed position so that the device can be repositioned within the heart of the patient, or removed completely as desired.

Furthermore, although each of the above embodiments describes a method of collapsing the left atrial appendage by pushing or pulling together the sides of the left atrial appendage, as a further refinement, it is contemplated that a vacuum can be used to remove blood from the left atrial appendage after the occluding portion seals the orifice, which also facilitates the collapsing of the left atrial appendage. The vacuum can be applied through, for example, the catheter and/or needle used to position the atrial appendage closure device, or a separate catheter and/or needle. Similarly, by making use of openings or fenestrations on the catheter/needle, radio-opaque dyes can be injected into the patient to check the positioning of the device and the integrity of the seal provided by the device. Similarly, it is contemplated that radio opaque marks can be included on the device itself to improve visibility and positioning during implantation.

The embodiments described above are only a few of the contemplated configurations and it should further be understood that, in some embodiments, the occluding member and/or the anchoring member can be constructed such that the surfaces assume various shapes to accommodate the anatomy of a particular heart and/or to accommodate a desired application. For example, in certain embodiments, an occluding member can include an outer surface that is convex and an inner surface that is concave. In certain other embodiments an occluding member can include an outer surface that is concave and an inner surface that is convex. In still other embodiments, the outer surface, the inner surface, or both can also be substantially flat. The anchoring portion similarly can have an outer surface or inner surface that is convex, concave, or flat regardless of the configuration of the occluding member.

The above-described atrial appendage closure devices and related methods of occluding an atrial appendage, which allow for a left atrial appendage of a heart to be completely sealed off from the left atrium, are important both for preventing clot formation that may otherwise occur with atrial fibrillation and for minimizing surgery-related complications that frequently occur in left atrial appendage occlusion therapy. Further, at least some of the devices of the presently-disclosed subject matter minimize the risk of puncturing portions of a heart during surgical placement as no barbs or similar anchoring mechanisms are inserted into the inside of the left atrial appendage. Moreover, the devices of the presently-disclosed subject matter can be provided in one size to thereby eliminate any patient-to-patient variability that is often observed with current atrial appendage closure devices and, in particular, pharmaceutical agent dosing. Thus, the atrial appendage closure devices of the presently-disclosed subject matter provide not only desirable alternatives to current device or pharmaceutical agent-based therapies, with the added benefit that complications arising from the implantation of the device are minimized.

Throughout this document, various references are mentioned. All such references are incorporated herein by reference, including the references set forth in the following list:

REFERENCES

1. Atrial Fibrillation Fact Sheet. February 2010. Centers for Disease Control and Prevention. 3 Apr. 2012.
2. Go A S, Hylek E M, Phillips K A, Chang Y, Henault L E, Shelby J V and Singer D E. Prevalence of Diagnosed Atrial Fibrillation in Adults: National Implications for Rhythm Management and Stroke Prevention: the Anticoagulation and Risk Factors in Atrial Fibrillation (Atria) Study. *Journal of the American Medical Association* 2001; 285: 2370-2375.
3. Wolf P A, Abbott R D, and Kannel W B. Atrial fibrillation as an Independent factor for stroke: The Framingham study. Stroke; 1991; 22:983-988.
4. Pearce L A, Hart R G and Halperin J L. Assessment of Three Schemes for Stratifying Stroke Risk in Patients with Nonvalvular Atrial Fibrillation. *The American Journal of Medicine* 2000; 109:45-51.
5. Aronow W S. Management of the Older Person With Atrial Fibrillation. *Journal of Gerontology: Medical Sciences* 2002; 57A:M352-M363.
6. Savelieva I, Bajpai A and Camm A J. Stroke in atrial fibrillation: Update on pathophysiology, new antithrombotic therapies, and evolution of procedures and devices. *Annals of Medicine* 2007; 39:371-391.
7. Jais P, Haissaguerre M, Shah D C, Chouairi S, Gencel L, Hocini M, and Clementy J. A Focal Source of Atrial Fibrillation Treated by Discrete Radiofrequency Ablation. *Circulation*. 1997; 95:572-576.
8. Go A S, Hylek E M, Borowsky L H, Phillips K A, Selby J V and Singer D E. Warfarin Use among Ambulatory Patients with Nonvalvular Atrial Fibrillation: The Anticoagulation and Risk Factors in Atrial Fibrillation (Atria) Study. *Annals of Internal Medicine* 1999; 131:927-934.
9. Mendelson G, and Aronow W S. Underutilization of Warfarin in Older Persons with Chronic Nonvalvular Atrial Fibrillation at High Risk for Developing Stroke. *Journal of the American Geriatrics Society* 1998; 46:P1423-P1424.
10. Hart R G, Benavente O, McBride R and Pearce L A. Antithrombotic Therapy To Prevent Stroke in Patients with Atrial Fibrillation: A Meta-Analysis. *Annals of Internal Medicine* 1999; 131:492-501.
11. Hylek E M, Go A S, Chang Y, Jensvold N G, Henault L E, Selby J V, et al. Effect of intensity of oral anticoagulation on stroke severity and mortality in atrial fibrillation. N Engl J Med. 2003; 349:1019-26.
12. Nieuwlaat R, Capucci A, Lip G Y, Olsson S B, Prins M H, Nieman F H, et al.; Euro Heart Survey Investigators. Antithrombotic treatment in real-life atrial fibrillation patients: a report from the Euro Heart Survey on Atrial Fibrillation. Eur Heart J. 2006; 27:3018-26.
13. McCormick D, Gurwitz J H, Goldberg R J, Becker R, Tate J P, Elwell A, et al. Prevalence and quality of warfarin use for patients with atrial fibrillation in the long-term care setting. Arch Intern Med. 2001; 16:2458-63.
14. Sarawate C, Sikirica M V, Willey V J, Bullano M F, Hauch O. Monitoring anticoagulation in atrial fibrillation. J Thromb Thrombolysis. 2006; 21:191-8.
15. Singer D E, Albers G W, Dalen J E, Go A S, Halperin J L, and Manning W J. Antithrombotic therapy in atrial fibrillation: the Seventh ACCP Conference on Antithrombotic and Thrombolytic Therapy. *Chest* 2004; 126:429S-56S.
16. Risk factors for stroke and efficacy of antithrombotic therapy in atrial fibrillation. Analysis of pooled data from five randomized controlled trials. *Archives of Internal Medicine* 1994; 154:1449-57.
17. Atwood J E, and Albers G W. Anticoagulation and atrial fibrillation. *Herz* 1993; 18:27-38.
18. Gullov A L, Koefoed B G, and Petersen P. Bleeding During Warfarin and Aspirin Therapy in Patients With Atrial Fibrillation: The Afasak 2 Study. *Archives of Internal Medicine* 1999; 159:1322-1328.
19. Liu M, Counsell C, Sandercock P. Anticoagulants for preventing recurrence following ischaemic stroke or transient ischaemic attack. (Cochrane Review). In: The Cochrane Library, Issue 1, 2002. Oxford: Update Software.
20. Desbiens D A. Deciding on Anticoagulating the Oldest Old with Atrial Fibrillation: Insights from Cost-Effectiveness Analysis. JAGS 2002; 50:863-869.
21. Aronow W S, Ahn C, Kronzon I, and Gutstein H. Incidence of new thromboembolic stroke in persons 62 years and older with chronic atrial fibrillation treated with warfarin versus aspirin. *Journal of the American Geriatrics Society* 1999; 47:366-8.
22. Lip G Y. Aspirin for Prevention of Stroke in Atrial Fibrillation. *Stroke* 2006; 37:1640.
23. Garcia D, and Hylek E. Stroke prevention in elderly patients with atrial fibrillation. *The Lancet* 2007; 370:460-461.
24. Lip G Y H and Boos C J. Antithrombotic treatment in atrial fibrillation. *Heart* 2006; 92:155-161.
25. Jailer A K. Warfarin reduced major stroke more than aspirin in elderly patients with atrial fibrillation in primary care. *Evidence Based Medicine* 2007; 12:172.
26. Kamath S, Blann A D, Chin B S, Lip G Y. A prospective randomized trial of aspirin-clopidogrel combination therapy and dose-adjusted warfarin on indices of thrombogenesis and platelet activation in atrial fibrillation. J Am Coll Cardiol. 2002; 40:484-90.
27. Lorenzoni R, Lazzerini G, Cocci F, De Caterina R. Shortterm prevention of thromboembolic complications in patients with atrial fibrillation with aspirin plus clopidogrel: the Clopidogrel-Aspirin Atrial Fibrillation (CLAAF) pilot study. Am Heart J. 2004; 148:e6.
28. ACTIVE Writing Group on behalf of the ACTIVE Investigators; Connolly S, Pogue J, Hart R, Pfeffer M, Hohnloser S, Chrolavicius S, et al. Clopidogrel plus aspirin versus oral anticoagulation for atrial fibrillation in the Atrial fibrillation Clopidogrel Trial with Irbesartan for prevention of Vascular Events (ACTIVE W): a randomized controlled trial. Lancet. 2006; 367:1903-12.
29. Healey J, Hart R, Pogue J, Yusuf S, Pfeffer M, Hohnloser S, et al., on behalf of The ACTIVE-W Investigators. Effect of underlying risk of stroke on treatment effects in the ACTIVEW Trial. (Abstract). Eur Heart J. 2006; 27 Supplement: Abstract P451.
30. Perzborn E, Roehrig S, Straub, A, Dagmar K, Mueck W, and Laux V. Rivaroxaban: A new oral factor Xa inhibitor. Arteriosclerosis, Thrombosis, and Vascular Biology. 2010; 30:376-381.
31. Eriksson B, Quinlan D, Weitz J. Comparative Pharmacodynamics and Pharmacokinetics of oral direct thrombin and Factor Xa inhibitors in development. Clinical Pharmacokinetics 2009: 48: 1-22.
32. Bayard Y L, Ostermayer S H, Hein R, Skowasch M, Buscheck F, Baranowski A, Heinisch C, Sievert H. Percutaneous devices for stroke prevention. Cardiovascular Revascularization Medicine. 2007:8:216-225.
33. Hanna I R, Kolm P, Martin R, Reisman M, Gray W and Block P C. Left atrial structure and function after percutaneous left atrial appendage transcatheter occlusion (PLAATO): Six-month echocardiographic follow-up. *Journal of the American College of Cardiology* 2004; 43:1868-72.
34. Nakai T, Lesh M D, Gerstenfeld E P, Virmani R, Jones R and Lee R J. Percutaneous Left Atrial Appendage Occlusion (PLAATO) for Preventing Cardioembolism: First Experience in Canine Model. *Circulation* 2002; 105:2217-2222.
35. Ostermayer S H, Reisman M, Kramer P H, Matthews R V, Gray W A, Block P C, Omran H, Bartorelli A L, Bella P D, Mario C D, Pappone C, Casale P N, Moses J W, Poppas A, Williams D O, Meier B, Skanes A, Teirstein P S, Lesh M D, Nakai T, Bayard Y, Billinger K, Trepels T, Krumsdorf U, and Sievert H. Percutaneous Left Atrial Appendage Transcatheter Occlusion (PLAATO System) to Prevent Stroke in High-Risk Patients With Non-Rheumatic Atrial Fibrillation: Results From the International Multi-Center Feasibility Trials. Journal of the American College of Cardiology 2005; 46:9-14.
36. Sievert H, Lesh M D, Trepels T, Omran H, Bartorelli A, Bella P D, Nakai T, Reisman M, DiMario C, Block P, Kramer P, Fleschenberg D, Krumsdorf U, and Scherer D. Percutaneous Left Atrial Appendage Transcatheter Occlusion to Prevent Stroke in High-Risk Patients With Atrial Fibrillation: Early Clinical Experience. *Circulation* 2002; 105:1887-1889.
37. Fountain R B, Holmes D R, Chandrasekaran K, Packer D, Asirvatham S, Tassel R V and Turi Z. The Protect A F (Watchman Left Atrial Appendage System for Embolic Protection in Patients with Atrial Fibrillation) Trial. *American Heart Journal* 2006; 151:956-61.
38. Sick P B, Schuler G, Hauptmann K E, Grube E, Yakubov S, Turi Z G, Mishkel G, Almany S, and Holmes D R. Initial Worldwide Experience with the WATCHMAN Left Atrial Appendage System for Stroke Prevention in Atrial Fibrillation. *Journal of the American College of Cardiology* 2007; 49:1490-5.
39. Sievert H and Bayard Y L. Percutaneous closure of the left atrial appendage: A major step forward. J Am Coll Cardiol Intv, 2009; 2:601-602.
40. Block P C. Watching the WATCHMAN. J Am Coll Cardiol, 2007; 49:1496-1497.
41. Maisel W H. Left atrial appendage occlusion—closure or just the beginning. New England Journal of Medicine, 2009.
42. Sick P B, Schuler G, Hauptmann K E, et al (April 2007). "Initial worldwide experience with the WATCHMAN left atrial appendage system for stroke prevention in atrial fibrillation". *J. Am. Coll. Cardiol.* 49 (13):1490-5
43. Onalan O and Crystal E. Left Atrial Appendage Exclusion for Stroke Prevention in Patients With Nonrheumatic Atrial Fibrillation. *Stroke* 2007; 38:624-630.
44. Ailawadi G, Gerdisch M W, Harvey R L, Hooker R L, Damiano R J Jr, Salamon T, and Mack M J. Exclusion of the left atrial appendage with a novel device: early results of a multicenter trial. *J Thorac Cardiovasc Surg.* 2011; 142(5): 1002-9.
45. Payne K A, Huybrechts K F, Caro J J, Craig Green T J, Klittich W S. Long term cost-of-illness in stroke: an international review. Pharmacoeconomics. 2002; 20:813-25.
46. Lafata J E, Martin S A, Kaatz S, Ward R E. The cost effectiveness of different management strategies for patients on chronic warfarin therapy. *J Gen Intern Med.* 2000; 15:31-7.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of occluding a left atrial appendage of a heart, comprising:
   positioning in the left atrial appendage (LAA) a closure device including an occluding portion and an anchoring portion, wherein the occluding portion has a distal surface and a proximal surface opposite the distal surface, wherein the occluding portion is moveable between a closed retracted position and a deployed position;

securing the anchoring portion to an inside wall of the LAA;

deploying the occluding portion inside a left atrium of the heart such that the occluding portion provides a seal between the LAA and the left atrium of the heart; and moving one or more elements of the anchoring portion and the occluding portion towards one another so as to shrink or collapse a volume defined by the LAA.

2. The method of claim 1, further comprising a step of securing the anchoring portion to the occluding portion.

3. The method of claim 1, wherein the step of securing the anchoring portion to the inside wall of the LAA is performed while the occluding portion is in the closed position.

4. The method of claim 1, wherein the step of securing the anchoring portion to the inside wall of the LAA is performed while the occluding portion is in the deployed position.

5. The method of claim 1, wherein the anchoring portion has a proximal end connected to the proximal surface of the occluding portion and a distal end positioned away from the proximal surface of the occluding portion, and wherein the step of securing the anchoring portion to the inside wall of the LAA comprises screwing the distal end of the anchoring portion into the inside wall of the LAA.

6. The method of claim 1, wherein the inside wall of the LAA to which the anchoring portion is secured is opposite an orifice between the LAA and the left atrium and wherein the step of moving comprises pulling the anchoring portion towards the orifice between the LAA and the left atrium until the inside wall of the LAA is positioned adjacent to the orifice.

7. The method of claim 1, wherein said percutaneously positioning step includes using a transseptal approach via a femoral vein of a subject.

8. The method of claim 7, wherein, during the step of percutaneously positioning, the closure device is positioned within a catheter with the occluding portion and the anchoring portion both in the closed position.

9. The method of claim 8, wherein the step of deploying the occluding portion inside the left atrium comprises removing the occluding portion from the catheter.

10. The method of claim 8, wherein the anchoring portion is movable between a closed position and a deployed position, and the method further comprises a step of deploying the anchoring portion inside the LAA of the heart before securing the anchoring portion to the inside wall of the LAA.

11. The method of claim 1, wherein the step of securing the anchoring portion to the inside wall of the LAA comprises deploying the anchoring member within the LAA, and wherein the step of moving comprises drawing together the anchoring portion and the occluding portion.

12. The method of claim 7, wherein the step of deploying the anchoring portion inside the LAA comprises removing the anchoring portion from a catheter.

* * * * *